United States Patent
Huberman

(10) Patent No.: US 6,673,623 B1
(45) Date of Patent: Jan. 6, 2004

(54) METHODS AND COMPOSITIONS THAT CONTROL LIPID PRODUCTION

(75) Inventor: Eliezer Huberman, LaGrange, IL (US)

(73) Assignee: Novocure, Inc., LaGrange, IL (US)

(*) Notice: Subject to any disclaimer, the term of this patent is extended or adjusted under 35 U.S.C. 154(b) by 87 days.

(21) Appl. No.: 09/660,107

(22) Filed: Sep. 12, 2000

(51) Int. Cl.⁷ .......................... G01N 33/00; C12N 11/02
(52) U.S. Cl. .......................... 436/86; 436/63; 436/151; 436/805; 435/40.5; 435/69.7; 435/70.1; 435/325
(58) Field of Search ............... 435/40.5, 69.7, 435/70.1, 325; 436/63, 86, 151, 805

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,642,334 A | 2/1987 | Moore et al. |
| 4,736,866 A | 4/1988 | Leder et al. |
| 4,816,567 A | 3/1989 | Cabilly et al. |
| 4,818,763 A | 4/1989 | Rusch et al. |
| 5,112,608 A | 5/1992 | Scott et al. |
| 5,162,215 A | 11/1992 | Bosselman et al. |
| 5,182,257 A | 1/1993 | Zeppezauer et al. |
| 5,187,089 A | 2/1993 | Scott et al. |
| 5,196,304 A | 3/1993 | Kanost et al. |
| 5,304,482 A | 4/1994 | Sambrook et al. |
| 5,376,640 A | 12/1994 | Miyazaki et al. |
| 5,411,956 A | 5/1995 | Miyazaki et al. |
| 5,449,757 A | 9/1995 | Serrero |
| 5,457,090 A | 10/1995 | Scott et al. |
| 5,486,602 A | 1/1996 | Sambrook et al. |
| 5,489,742 A | 2/1996 | Hammer et al. |
| 5,495,001 A | 2/1996 | McGrogan et al. |
| 5,550,042 A | 8/1996 | Sambrook et al. |
| 5,550,316 A | 8/1996 | Mintz |
| 5,573,933 A | 11/1996 | Seamark et al. |
| 5,595,885 A | 1/1997 | Stetler-Stevenson et al. |
| 5,614,396 A | 3/1997 | Bradley et al. |
| 5,625,125 A | 4/1997 | Bennett et al. |
| 5,648,061 A | 7/1997 | Bernstein et al. |
| 5,648,248 A | 7/1997 | Zenke et al. |
| 5,698,671 A | 12/1997 | Stetler-Stevenson et al. |
| 5,700,924 A | 12/1997 | Braxton et al. |
| 5,728,564 A | 3/1998 | Sambrook et al. |
| 5,741,957 A | 4/1998 | Deboer et al. |
| 5,846,734 A | 12/1998 | Serrero |
| 5,866,413 A | 2/1999 | Sambrook et al. |
| 5,872,152 A | 2/1999 | Brown et al. |
| 5,908,831 A | 6/1999 | Bandman et al. |
| 5,929,210 A | 7/1999 | Braxton et al. |
| 5,945,297 A | 8/1999 | Gadbut |
| 5,981,220 A | 11/1999 | Ni et al. |
| 6,057,109 A | 5/2000 | Tartaglia |
| 6,103,496 A | 8/2000 | Brash et al. |
| 6,110,723 A | 8/2000 | Powell |
| 6,111,090 A | 8/2000 | Gorman et al. |

OTHER PUBLICATIONS

Allen, J.B., (1995) et al."Finding Prospective Partners in the Library: the Two–Hybrid System and Phage Display find a Match." *TIBS* 20: 511–516.

Aten, R.F. and Behrman, H.R. (1989) "A Gonadotropin–Releasing Hormone–Binding Inhibitor from Bovine Ovaries," *J Biol Chem* 264(19): 11065–11071.

Bacus, S.S., et al. (1990) "Differentiation of Cultured Human Breast Cancer Cells (AU–565 and MCF-7) Associated with Loss of Cell Surface HER–2/neu Antigen." *Mol Carcinogenesis* 3: 350–362.

Barzilai, N. and Gupta, G. (1999) "Revisiting the Role of Fat Mass in the Life Extension Induced by Caloric Restriction," *J Gerontol A Biol Sci Med Sci* 54(3): B89–96.

Bastard, J.P. and Pieroni, L. (1999) "Plasma Plasminogen Activator Inhibitor 1, Insulin Resistance and Android Obesity," *Biomed Pharmacother* 53(10): 455–61.

Bennett, C.F. (1998) "Antisense Oligonucleotides: is the Glass Half Full or Half Empty?" *Biochem Pharmacol* 55(1): 9–19.

Bhalerao, J. et al. (1995) "Molecular Cloning Characterization, and Genetic Mapping of the cDNA Coding for a Novel Secretor Protein of Mouse," *J Biol Chem* 270(27): 16385–16394.

Boyer, P.M. and Hsu, J.T. (1993) "Protein Purification by Dye–ligand Chromatography," *Adv Biochem Eng Biotechnol* 49: 1–44.

Brenneman, D.E., et al. (1998) "VIP Neurotophism in the Central Nervous System: Multiple Effectors and Identification of a Femtomolar–Acting Neutoprotective Peptide," *Ann N Y Acad Sci* 865: 207–12.

Choi, B.H., et al. (1995) "Decreases in Protease Nexins in Alzheimer's Disease Brain." *Neurobiol Aging* 4: 557–62.

CLONTECH Laboratories, Inc. (1999) Matchmaker (GAL4 Two–Hybrid System 3 & Libraries User Manual PT3247–1 (PR94575).

Constantinou, A. et al. (1990) "Induction of Differentiation and DNA Strand Breakage in Human HL–60 and K–562 Leukemia Cells by Genistein." *Cancer Res* 50: 2618–2624.

(List continued on next page.)

*Primary Examiner*—Long V. Le
*Assistant Examiner*—Changhwa J. Cheu
(74) *Attorney, Agent, or Firm*—Alice O. Martin; Barnes & Thornburg

(57) ABSTRACT

The present invention relates generally to the use of lipogenins, proteins, e.g. human extra-cellular matrix protein 1 (ECM-1), human glia-derived nexin I alpha protein (NP-I), human tissue inhibitor of metalloproteinase-2 (TIMP-2) and human histone H2A (H2A) singly or in various combinations to control lipogenesis in a mammal.

4 Claims, 16 Drawing Sheets

OTHER PUBLICATIONS

Cunningham, D.D. and Donovan, F.M. (1997) "Regulation of Neurons and Astrocytes by Thrombin and Protease Nexin–1. Relationship to Brain Injury." *Adv Exp Med Biol* 425: 67–75.

Diaz–Nido, J., et al. (1991) "Addition of Protease Inhibitors to Culture Medium of Neuroblastoma Cells Induces both Neurite Outgrowth and Phosphorylation of Microtubule–Associated Protein MAP–1B." *J Cell Sci* (Pt 3): 409–14.

Doenecke, D., et al. (1997) "Histones: Genetic Diversity and Tissue–Specific Gene Expression" *Histochem Cell Biol* 107(1): 1–10.

Endo, T., (1996) "Fractionation of Glycoprotein–derived Oligosaccharides by Affinity Chromatography using Immobilized Lectin Columns." *J Chromatogr A* 720(1–2): 251–61.

Fiorucci, L., et al., (1997) "Histone–Tryptase Interaction: H2A N–Terminal Tail Removal and Inhibitory Activity." *Archives of Biochem and Biophysics* 347(2): 229–234.

Frederickson, R.M. (1998) "Macromoleculas Matchmaking: Advances in Two–Hybrid and Related Technologies." *Current Opinion in Biotech* 9: 90–96.

Gamberucci, A., et al. (1998) "Histones and Basic Polypeptides Activate Ca2+/cation Influx in Various Cell Types." *Biochem J* 331 (Pt 2): 623–30.

Giometti, C.S., et al. (1995) "Analysis of Proteins from Human Breast Epithelial Cells using Two–dimensional Gel Electrophoresis." [Submitted to Electrophoresis Feb. 8, 1995].

Goldberg, G.J. et al. (1989) "Human 72–Kilodalton Type IV Collagenase forms a Complex with a Tissue Inhibitor of Metalloprotease Designated TIMP–2." *Proc Natl Acad Sci USA* 86(21): 8207–11.

Gurwitz, D. and Cunningham, D.D. (1988) "Thrombin Modulates and Reverses Neuroblastoma Neurite Outgrowth." *Proc Natl Acad Sci USA* 85(10): 3440–4.

HHMI Biopolymer/Keck Foundation Biotechnology Resource Laboratory at Yale University: Sample Submittal and Ordering; Description of Protein Analysis Services; More Information on Matrix Assisted Laser Desorption Ionization (MALDI) Mass Spectrometry.

Houenou, L.L., et al. (1999) "Pigment Epithelium–derived Factor Promotes the Survival and Differntiation of Developing Spinal Motor Neurons." *J Comp Neurol* 412(3): 506–14.

Huberman, E., et al. (1979) "Stimulation of Differentiated Functions in Human Melanoma Cells by Tumor–Promoting Agents and Dimethyl Sulfoxide." *Cancer Res* 39: 2618–2624.

Izant, J.G. and Weintraub, H. (1985) "Constitutive and Conditional Suppression of Exogenous and Endogenous Genes by Anti–sense RNA." *Science* 229(4711): 345–52.

Janis, I.J. and Regnier, F.E. (1988) "Immunological–Chromatographic Analysis." *J Chromatogr* 444: 1–11.

Kiguchi, K., et al. (1990) "Induction of Cell Differentiation in Melanoma Cells by Inhibitors of IMP Dehydrogenase: Altered Patterns of IMP Dehydrogenase Expression and Activity." *Cell Growth & Differentiation* 1: 259–270.

Klebe, G. (2000) "Recent Developments in Structure–Based Drug Design." *J Mol Med* 78(5): 269–81.

Kleiner, D.E. and Stetler–Stevenson, W.G. (1999) "Matrix Metalloproteinases and Metastasis." *Cancer Chromother Pharmacol* 43: S42–51.

Knauer, M.F. et al. (1997) "The Efficient Catabolism of Thrombin–Protease Nexin 1 Complexes is a Synergistic Mechanism that Requires Both the LDL Receptor–Related Protein and Cell Surface Heparins." *J Biol Chem* 272(46): 29039–45.

Lonnberg, H. and Vuorio, E. (1996) "Towards Genomic Drug Therapy with Antisense Oligonucleotides." *Ann Med* 28(6): 511–22.

Louters, L.L. et al. (1993) "Histone H4 Stimulates Glucose Transport Activity in Rat Skeletal Muscle." *Biochem J* 295: 549–553.

Mathews, D.H. et al. (1999) "Expanded Sequence Dependence of Thermodynamic Parameters Improves Prediction of RNA Secondary Structure." *J Med Biol* 288(5): 911–40.

Mbebi, C. et al. (1999) "Protease Nexin 1 Expression is Up–Regulated in Human Skeletal Muscle by Injury–Related Factors." *J Cell Physiol* 179(3): 305–14.

McCroskey, M.C. et al. (1989) "Insulin–Like Effects of Histones H3 and H4 on Isolated Rat Adipocytes." *Biochemica et Biophysica Acta* 1011: 212–219.

Monteith, D.K. and Levin A.A. (1999) "Synthetic Oligonucleotides: The Development of Antisense Therapeutics." *Toxicol Pathol* 27(1): 8–13.

Nagase, H. (1998) "Cell Surface Activation of Progelatinase A (proMMP–2) and Cell Migraiton." *Cell Res* 8(3): 179–86.

NCBI National Library of Medicine PubMed Searches: extra cellular matrix protein I: h2a and hormones and human:histone and obesity: hormone and h2a:human extracellular matrix protein 1 and adipcy: phage display technology and hoess; timp–2 and differentiation.

NCBI National Library of Medicine: PubMed Search Results. Aug. 22, 2000: Crisp, R.J., et al.; Camani, C., et al.; Mbebi, C., et al.: Knauer, M.F., et al.: Sternlicht, M.D., et al.: Turgeon, V.L., et al.: Shao, Z.M., et al.: Kasza, A., et al.: Djie, M.Z., et al.: Scandura, J.M. et al.: Tucker, H.M., et al. Conese M. et al.: Carter, R.E., et al.: Rao, C.N. et al.: Hornebeck, W., et al.: Conese, M., et al.: Akaaboune, M., et al.

NCBI: Nucleotide: GenBank Search Results. Aug. 23, 2000.

Okabe–Kado, J. et al. (1981) "Effects of Histone Fractions on Induction of Differentiation of Cultured Mouse Myeloid Leukemia Cells." *Cancer Res* 41(5): 1997–2002.

Pang, J.H. and Chen, K.Y. (1994) "Global Change of Gene Expression at Late G1/S Boundary May Occur in Human IMR–90 Diploid Fibroblasts During Senescence." *J Cell Physiol* 160(3): 531–8.

Park, C.B., et al. (1996) "A Noval Antimicrobial Peptide from BUFO bufo Gargarizans." *Biochem and Biophys Research Communications* 218: 408–413.

Park, I.Y., et al. (1998) "Parasin I, an Antimicrobial Peptide Derived from Histone H2A in the Catfish. Parasilurus Asotus." *FEBS Letters* 437: 258–262.

Reichhart, R. et al. (1985) "Preparations of Homeostatic Thymus Homrone Consist Predominantly of Histones 2A and 2B and Suggest Additional Histone Functions." *Proc Natl Acad Sci USA* 82: 4871–4875.

Rettenberger, P.M. et al. (1999) "Ligand Binding Properties of the Very Low Density Lipoprotein Receptor, Absence of the Third Complement–Type Repeat Encoded by Exon 4 is Associated with Reduced Binding of Mr 40,000 Receptor–Associated Protein." *J Biol Chem* 274(13): 8973–80.

Ryffel, B. et al. (1982) "Differentiation of Human T–Lymphoid Leukemia Cells into Cells that Have a Suppressor Phenotype is Induced by Phorbol 12–Myristate 13–Acetate." *Proc Natl Acad Sci USA* 79: 7336–7340.

Samad, F. and Loskutoff, D.J. (1997) "The Fat Mouse: A Powerful Genetic Model to Study Elevated Plasminogen Activator Inhibitor 1 in Obesity/NIDDM." *Thromb Haemost* 78(1): 652–5.

Search Results for Sequence of ECM–1b, NP–1, TIMP–2 and H2A.

Semizarov, D. et al. (1998) "A Lineage–Specific Protein Kinase Crucial for Myeloid Maturation." *Proc Natl Acad Sci USA* 95: 15412–15417.

Smits, P. et al. (1997) "The Human Extracellular Matrix Gene 1 (ECM 1): Genomic Structure, cDNA Cloning, Expression Pattern, and Chromosomal Localization." *Genomics* 45: 487–495 Article No. GE974918.

Smits, P., et al. (1999) "Molecular Cloning and Characterization of the Mouse Ecm1 Gene and its 5' Regulatory Sequences." *Gene* 226: 253–261.

Smyth, M.S. and Martin, J.H. (2000) "X Ray Crystallography." *Mol Pathol* 53(1): 8–14.

Sommer, J., et al. (1987) "cDNA Sequence Coding for a Rat Glia–Derived Nexin and its Homology to Members of the Serpin Superfamily." *Biochem* 26(20): 6407–10.

Sonoda, T. et al. (1999) "The mRNA for Protease Nexin–1 is Expressed in Human Dermal Papilla Cells and its Level is Affected by Androgen." *J Invest Dermatol* 113(3): 308–13.

Spielholz, C., et al. (1995) "Granulocyte–Macrophage Colony–Stimulating Factor Signals for Increased Glucose Uptake in Human Melanoma Cells." *Blood* 85(4): 973–80.

Stein, C.A. (2000) "Is Irrelevant Cleavage the Price of Antisense Efficacy?" *Pharmacol Ther* 85(3): 231–6.

Stetler–Stevenson, W.G., et al. (1989) "Tissue Inhibitor of Metalloproteinase (TIMP–2). A New Member of the Metalloproteinase Inhibitor Family." *J Biol Chem* 264(29): 17374–8.

Strehlow, D., et al. (1999) "A Potential Role for Protease Nexin 1 Overexpression in the Pathogenesis of Scleroderma." *J Clin Invest* 103(8): 1179–90.

Thelin–Jarnum, S., et al. (1999) "Identification of Genes Differentially Expressed in TLS–CHOP Carrying Myxoid Liposarcomas." *Int J Cancer* 83(1): 30–3.

Tonetti, D.A., et al. (1994) "Protein Kinase C–$\beta$ is Required for Macrophage Differentiation of Human HL–60 Leukemia Cells." *J Biol Chem* 269(37): 23230–23235.

Tsuneishl, S. (1992) "Regulation of Neurite Outgrowth through Protein Kinase C and Protease Nexin–1 in Neuroblastoma Cell." *Kobe J Med Sci* 38(3): 147–59.

Turgeon, V.L. and Houenou, I.J. (1997) "The Role of Thrombin–Like (Serine) Proteases in the Development, Plasticity and Pathology of the Nervous System." *Brain Res Brain Res Rev* 25(1): 85–95.

Varga, L.V., et al. (1999) "Antisense Strategies: Functions and Applications in Immunology." *Immunol Lett* 69(2): 217–24.

Vidal, M. and Legrain, P. (1999) "Yeast Forward and Reverse 'n'–Hybrid Systems." *Nuc Aci Re* 27(4): 919–929.

Werb, Z and Chin, J.R. (1998) "Extracellular Matrix Remodeling During Morphogenesis." *Ann N Y Acad Sci* 857: 110–8.

Wickstrom, E.L., et al. (1988) "Human Promyelocytic Leukemia HL–60 Cell Proliferation and c–myc Protein Expression are Inhibited by an Antisense Pentadecadeoxynucleotide Targeted Against c–myc mRNA." *Proc Natl Acad Sci USA* 85(4): 1028–32.

FIGURE 4

```
  1  mnwhlplfll asvtlpsics hfnplsleel gsntgiqvfn qivksrphdn ivisphgias
 61  vlgmlqlgad grtkkqlamv mrygvngvgk ilkkinkaiv skknkdivtv anavfvknas
121  eievpfvtrn kdvfqcevrn vnfedpasac dsinawvkne trdmidnlls pdlidgvltr
181  lvlvnavyfk glwksrfqpe ntkkrtfvaa dgksyqvpml aqlsvfrcgs tsapndlwyn
241  fielpyhges ismlialpte sstplsaiip histktidsw msimvpkrvq vilpkftava
301  qtdlkeplkv lgitdmfdss kanfakitrs enlhvshilq kakievsedg tkasaattai
361  liarssppwf ivdrpflffi rhnptgavlf mgqinkp(SEQ ID NO: 1)
```

FIGURE 5

```
  1  msgrgkqggk arakaktrss raglqfpvgr vhrllrkgny aervgagapv ylaavleylt
 61  aeilelagna ardnkktrii prhlqlairn deelnkllgk vtiaqggvlp niqavllpkk
121  teshhkakgk(SEQ ID NO: 2)
```

FIGURE 6

```
  1  msgrgkqggk arakaktrss raglqfpvgr vhrllrkahy servgagapv ylaavleylt
 61  aeilelagna ardnkktrii prhlqlairn deelnkllgr vtiaqggvlp niqavllpkk
121  teshhkakgk (SEQ ID NO: 3)
```

FIGURE 7

```
  1   maggkagkds gkaktkavsr sqraglqfpv grihrhlksr ttshgrvgat aavysaaile
 61   yltaevlela gnaskdlkvk ritprhlqla irgdeeldsl ikatiagggv iphihkslig
121   kkgqqktv   (SEQ ID NO: 4)
```

FIGURE 3

```
  1  msgrgktggk arakaksrss raglqfpvgr vhrllrkghy aervgagapv ylaavleylt
 61  aeilelagna ardnkktrii prhlqlairn deelnkllgg vtiaqggvlp niqavllpkk
121  tsatvgpkap sggkkatqas qey (SEQ ID NO: 5)
```

FIGURE 9

```
  1  msgrgkqggk arakaksrss raglqfpvgr vhrllrkgny aervgagapv ymaavleylt
 61  aeilelagna ardnkktrii prhlqlairn deelnkllgk vtiaqggvlp niqavllpkk
121  teshhkakgk  (SEQ ID NO: 6)
```

FIGURE 10

```
  1  msgrgkqggk arakaksrss raglqfpvgr vhrllrkgny aervgagapv ylaavleylt
 61  aeilelagna ardnkktrii prhlqlairn deelnkllgr vtiaqggvlp niqavllpkk
121  teshhkakgk   (SEQ ID NO: 7)
```

FIGURE 11

```
  1  msgrgkqggk arakaktrss raglqfpvgr vhrllrkgny aervgagapv ylaavleylt
 61  aeilelagna ardnkktrii prhlqlairn deelnkllgk vtiaqggvlp niqavllpkk
121  teshhkakgk (SEQ ID NO: 8)
```

FIGURE 12

```
  1  msgrgkqggk arakaktrss raglqfpvgr vhrllrkgny aervgagapv ylaavleylt
 61  aeilelagna ardnkktrii prhlqlairn deelnkllgk vtiaqggvlp niqavllpkk
121  teshhkakgk  (SEQ ID NO: 9)
```

FIGURE 13

```
  1   msgrgkqggk arakaktrss raglqfpvgr vhrllrkgny aervgagapv ylaavleylt
 61   aeilelagna ardnkktrii prhlqlairn deelnkllgk vtiaqggvlp niqavllpkk
121   teshhkakgk  (SEQ ID NO: 10)
```

FIGURE 14

```
  1   mgaaartlrl alglllatl lrpadacscs pvhpqqafcn advvirakav sekevdsgnd
 61   iygnpikriq yeikqikmfk gpekdiefiy tapssavcgv sldvggkkey liagkaegdg
121   kmhitlcdfi vpwdtlsttq kkslnhryqm gceckitrcp mipcyisspd eclwmdwvte
181   kninghqakf facikrsdgs cawyrgaapp kqefldiedp  (SEQ ID NO: 11)
```

FIGURE 15

```
   1 cgcagcaaac acatccgtag aaggcagcgc ggccgccgag agccgcagcg ccgctcgccc
  61 gccgccccc accccgccgc cccgcccggc gaattgcgcc ccgcgcccct cccctcgcgc
 121 ccccgagaca aagaggagag aaagtttgcg cggccgagcg gggcaggtga ggagggtgag
 181 ccgcgcggga ggggcccgcc tcggcccgg ctcagccccc gcccgcgccc ccagcccgcc
 241 gccgcgagca gcgcccggac ccccagcgg cggccccgc ccgcccagcc ccccggcccg
 301 ccatgggcgc cgcggcccgc accctgcggc tggcgctcgg cctcctgctg ctggcgacgc
 361 tgcttcgccc ggccgacgcc tgcagctgct ccccggtgca cccgcaacag gcgttttgca
 421 atgcagatgt agtgatcagg gccaaagcgg tcagtgagaa ggaagtggac tctggaaacg
 481 acatttatgg caaccctatc aagaggatcc agtatgagat caagcagata aagatgttca
 541 aagggcctga gaaggatata gagtttatct acacggcccc ctcctcggca gtgtgtgggg
 601 tctcgctgga cgttgagga aagaaggaat atctcattgc aggaaaggcc gaggggacg
 661 gcaagatgca catcaccctc tgtgacttca tcgtgccctg ggacaccctg agcaccaccc
 721 agaagaagag cctgaaccac aggtaccaga tgggctgcga gtgcaagatc acgcgctgcc
 781 ccatgatccc gtgctacatc tcctccccgg acgagtgcct ctggatggac tgggtcacag
 841 agaagaacat caacgggcac caggccaagt tcttcgcctg catcaagaga agtgacggct
 901 cctgtgcgtg gtaccgcggc gcggcgcccc ccaagcagga gtttctcgac atcgaggacc
 961 cataagcagg cctccaacgc ccctgtggcc aactgcaaaa aaagcctcca agggtttcga
1021 ctggtccagc tctgacatcc cttcctggaa acagcatgaa taaaacactc atccc          (SEQ ID NO: 12)
```

FIGURE 16

```
  1  mgttaraalv ltylavasaa seggftatgq rqlrpehfqe vgyaappspp lsrslpmdhp
 61  dssqhgppfe gqsqvqppps qeatplqqek llpaqlpaek evgpplpqea vplqkelpsl
121  qhpneqkegt papfgdqshp epeswnaaqh cqqdrsqggw ghrldgfppg rpspdnlnqi
181  clpnrqhvvy gpwnlpqssy shltrqgetl nfleigysrc chcrshtnrl ecaklvweea
241  msrfceaefs vktrphwcct rqgearfscf qeeapqphyq lracpshqpd issglelpfp
301  pgvptldnik nichlrrfrs vprnlpatdp lqrellaliq lerefqrccr qgnnhtctwk
361  awedtldkyc dreyavkthh hlccrhppsp trdecfarra pypnydrdil tidisrvtpn
421  lmghlcgnqr vltkhkhipg lihnmtarcc dlpfpeqacc aeeekltfin dlcgprrniw
481  rdpalccyls pgdeqvncfn inylrnvalv sgdtenakgq geqgstggtn isstsepkee
541                                                        (SEQ ID NO: 13)
```

METHODS AND COMPOSITIONS THAT CONTROL LIPID PRODUCTION

BACKGROUND OF INVENTION

Previously known proteins were purified and found to have effects on lipogenesis. Control of these proteins by inhibitors or by antisense molecules, may be used to control obesity and other lipid-production related conditions in mammals.

Obesity is a major health problem in humans because it causes an increased risk for various diseases, including high blood pressure, diabetes, coronary heart disease, stroke, respiratory complications, some forms of cancer, and joint and back problems (Kopelman, 2000). An accepted international definition of an obese individual, is a person whose body mass index (weight divided by the square of the body's height) is 30 kg per meter square or higher (WHO, 1998). According to this definition, more than 20% of the U.S. population is currently obese. This high percentage is, most likely, due to an increased food intake, encouraged by the abundance, constant advertisement and low-price of high caloric foods.

Although increased food intake is the major contributor of obesity, its level is influenced by the genetic make-up, environment and life style of the affected individual (Hill and Peters, 1998). The influence of heredity can be deduced from the observation that obesity tends to run in families. Yet, better illustrations of the impact of genetics comes from studies of identical twins. Independent of their food intake and environment, such twins exhibit a similar weight gain and similar fat deposition sites (Bouchard et. al., 1990; Allison et. al., 1996). By means of a genome-wide linkage scan, it was recognized that humans have more than 40 potential obesity associated genetic loci (Perusse et. al., 1999), whereas, based on crosses between inbred strains, mice have more than 70 such loci (Barch et al., 2000). Because of the polygenic nature of obesity, the influence of the environment and the differences in life style, it was difficult to directly ascertain in humans the identity of specific obesity genes. Fortunately, because of the availability of obese mouse models and the evolutionary conservation of many genes between mice and humans, it was possible to characterize a number of obesity genes. The most studied of these are the ob gene, which encodes the adipocyte-derived hormone leptin, and the db gene, which encodes its receptor. It appears that the interactions of leptin and insulin with their corresponding receptors in the brain contribute to the regulation of food intake (Schwartz et al., 2000). However, obesity resulting from alterations in the structure of ob or db genes are rare (Montague, et al., 1997; Clement et al., 1997; Strobel et al., 1998). Other obesity genes derived from mouse models are the fat gene, which encodes carboxypeptidase E and the *agouti* gene, which encodes an antagonist of the alpha melanin-stimulating hormone and is associated with mouse far pigmentation (Barsh et al., 2000).

An important aspect of understanding obesity is identifying the processes that lead to the differentiation of progenitor cells into adipocytes (fat cells) and the characterization of the cellular signaling that brings about such differentiation. The development of immortal-mouse cell culture models during the seventies (Green and Kehinde, 1974) was a major catalyst for such an understanding. Most of the studies with these and related cell culture models focused on the nature and function of transcription factors involved in adipogenesis. Particular emphasis was on the CCAAT/enhancer binding protein family, peroxisome proliferator-activated response elements and adipocyte determination- and differentiation-dependent factors (Brun et al., 1996; Mandrup and Lane, 1997). In addition, these cell culture systems helped identify a number of natural inducers of adipocyte differentiation, predominantly including the insulin-like growth factor −1, the growth hormone and a number of corticosteroids (Cornelius et al., 1994; Ailhaud et al., 1994a; Ailhaud et al., 1994b; Smas and Sul, 1994). While these studies have helped to advance obesity research, there is still a need to identify circulatory factors that may directly affect adipocyte differentiation and consequent obesity, the fat reserves in the human body. Once identified, it may be possible by an appropriate inhibitions or regulation of these factors to alleviate obesity and its negative impact on health.

There are several molecules whose existence was previously known, but were not suspected of having any role in adipocyte differentiation. These include the human extracellular matrix protein 1 (ECM-1), human glia-derived nexin I alpha protein (NP-I), human histone H2A (H2A) and human tissue inhibitor of metaloproteinase-2 (TIMP-2).

ECM-1 was originally identified as an 85-kD protein secreted by an osteogenic (MN7) cell line from the mouse (Mathieu et al., 1994). This protein is encoded by a 1.9 kb mRNA, whereas the human form of this protein is encoded by a 1.8 kb mRNA. ECM-1 gene expression was detected in a number of tissues including brain, heart, kidney, lung and muscle. Besides, both mice and humans also have a shorter splice form of the gene; in the mouse a 1.4 kb mRNA and in the human a 1.5 kb mRNA. The shorter human splice form is primarily detected in human tonsils and skin (Bhalerao et al., 1995; Smits et al., 1997). The cellular function of these two splice forms is not known. Yet, recently it was reported that the level of the shorter transcript increases during human keratinocyte differentiation (Smits et al., 2000). An ECM-1 associated polypeptide was suggested for the treatment and/or prevention of skin diseases (U.S. Pat. No. 5,981,220).

Serine endopeptidases use serine as the nucleophile in peptide bond cleavage, and are involved in many cellular functions. (Barerett, 1986). In addition, there are specific protein families that effectively inhibit these proteases. NP-I, which is a glycoprotein with a mass of 43–50 kDa, belongs to such a family of inhibitors, termed serpins (Scott et al., 1983; Mbebi et al., 1999). This inhibitor, which is produced and released by different cells including fibroblasts, myotubes, glial cells and vascular smooth muscle cells, is found in serum but in minute amounts. Biologically, NP-I has been found to induce neuronal differentiation in culture (Diaz-Nido et al., 1992).

The matrix metalloproteinases are a family of zinc-dependent endoproteinases that degrade components of the extracellular matrix. These proteinases and their inhibitors, including TIMP-2, play a key role in normal physiological processes such as developmental programs of different tissues, cell migration, wound healing and angiogenesis as well as in pathological processes such as arthritis, atherosclerosis and tumor cell invasion and metastasis (Bode et al., 2000). As described in the present invention, TIMP-2, has a mass of about 25-kDa (Goldberg et al., 1989).

Histone H2A, which is a small basic protein, is an important component of chromatin composition and structure. In addition, H2A, which has many variants was reported to display hormone-like activities. For example, in anterior pituitary cells it behaves as a gonadotrophin-releasing hormone (Brown et al., 1998), in the thymus it acts as a homeostatic hormone (Reichhard et al., 1985), in luteinized ovarian cells it exhibits an anti-gonadotropic effect (Margolin et al., 1992), whereas in mammary cells it functions as a growth factor (Watanabe et al., 1996). H2A was also reported to induce cellular differentiation in myeloid leukemia cells (Okabe-Kado et al., 1981). In addition, H2A has been recommended for use as a stimulator of the immune response (U.S. Pat. No. 4,818,763).

The present invention describes the surprising identification of ECM-1, NP-1, H2A and TIMP-2 as lipogenins.

SUMMARY OF THE INVENTION

The present invention relates generally to the use of human lipogenins including extra-cellular matrix protein 1 (ECM-1), human glia-derived nexin I alpha protein (NP-1) human tissue inhibitor of metalloproteinase-2 (TIMP-2) and human histone H2A (H2A) singly or in various combinations to control lipogenesis. For the present invention a lipogenin is defined as a protein/peptide, or a mixture of proteins and/or peptides that induces cellular lipid (fat) droplet formation, which is due to the production and/or accumulation of cellular lipids in the droplets.

In particular, this invention relates to the use in lipogenesis of purified and isolated DNA sequences that encode ECM-1, NP-I, TIMP-2, or H2A, of expression products of these DNA sequences in transformed or transfected host cells, of recombinant and synthetic proteins and peptides having amino acids deduced from these DNA sequences, and of antibodies specific for such proteins and peptides, in controlling lipogenesis. In addition, this invention relates to the use of ECM-1, NP-I, TIMP-2 or H2A or a portion thereof, for the identification, isolation and characterization of binding sites responsible for the lipogenic effect of ECM-1, NP-I, TIMP-2 or H2A. This invention also relates to the use of lipogenic ECM-1, NP-I, TIMP-2, or H2A proteins or peptides, and the corresponding binding proteins or peptides in assays to identify drugs that modify the lipogenic action of these proteins or peptides. Modification of lipogenesis is a method to control obesity.

By "control" is meant herein, affecting the production of lipid droplets over controlled values in cells not control with a lipogenin.

BRIEF DESCRIPTION OF THE DRAWINGS

FIG. 4 is an amino acid sequence (SEQ ID NO: 1) of a human glia-derived nexin-1 alpha precursor. [Sommer et al., (1987) Biochemistry 26(20):6407–6410; McGrogan et al. (1988) Bio/Technology 6:172–177].

FIG. 5 is an amino acid sequence (SEQ ID NO: 2) of an H2A variant [Dobner et al. (1991) DNA Seq. 1(6):409–413; Albig and Doenecke (1997) Hum. Genet. 101(3):284–294].

FIG. 6 is an amino acid sequence (SEQ ID NO: 3) of an H2A variant [Zhong et al. (1983) Nucleic Acids Res. 11(21): 7409–7425; Albig et al., (1997)].

FIG. 7 is an amino acid sequence (SEQ ID NO: 4) of an H2A variant [Hatch and Bonner (1988) Nuc. Acids Res. 16:1113–1124].

FIG. 8 is an amino acid sequence (SEQ ID NO: 5) of an H2A variant [Manneroni et al. (1989) Nuc. Acids Res. 17(22):9113–9126; Bonner, (1989)];

FIG. 9 is an amino acid sequence (SEQ ID NO: 6) of an H2A variant [Manneroni et al. (1994) DNA Cell Biol. 13(2):161–170].

FIG. 10 is an amino acid sequence (SEQ ID NO: 7) of an H2A variant [Ruddy et al. (1997) direct submission].

FIG. 11 is an amino acid sequence (SEQ ID NO: 8) of an H2A variant [Albig et al. (1997) Gene 184(2):141–148; Hum. Genet. (1997) 101(3):284–294].

FIG. 12 is an amino acid sequence (SEQ ID NO: 9) of an H2A variant [Albig et al. (1997) Hum. Genet. 101(3): 284–294; Biol. Chem., 1999; Biol. Chem. 380(1):7–18].

FIG. 13 is an amino acid sequence (SEQ ID NO: 10) of an H2A variant [Albig et al., 1997, 1999].

FIG. 14 is an amino acid sequence (SEQ ID NO: 11) of a human tissue inhibitor of a metaloproteinase 2 precursor [Stettler-Stevenson et al., (1989) J. Biol. Chem. 264(29): 17374–17378; J. Biol. Chem. (1990) 265(23):13933–13938; Boone et al. (1990) DNAS 87(7):2800–2804; Leotta et al. (1991) Important Advances in Oncology 85–100; Osthues et al. (1992) FEBS lett. 296(1):16–20; DeClerk et al. (1992) Genomics 14(3):782–784; (1994) Gene 139(2):185–191; Hominoni et al. (1996) J. Biol. Chem. 27(41)25498–25505].

FIG. 15 is an amino acid sequence (SEQ ID NO: 12) of TIMP-2 [Stetter-Stevenson et al. (1989) J. Biol. Chem. 264(29):17374–17378].

FIG. 16 is an amino acid sequence (SEQ ID NO: 13) of the extracellular matrix protein [Smits et al. (1997) Genomics 45(3):487–495].

DETAILED DESCRIPTION OF THE INVENTION

Figure 1:
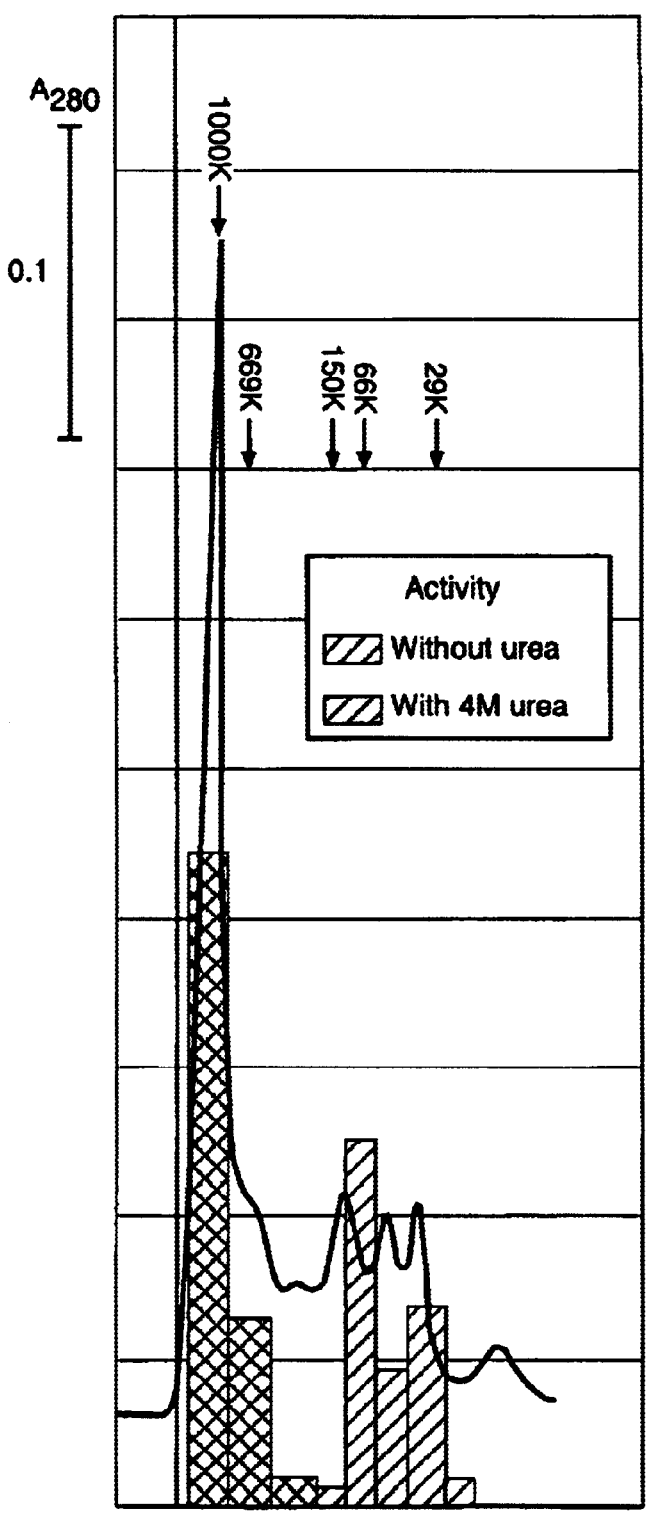
FIG. 1 shows size-exclusion chromatography of the active sample eluted from heparin resin by 0.5M NaCl; absorbence at 280 nm is indicated by a solid line whereas activity peaks are indicated by bars with (stripes) or without (crossbarred) urea; arrows indicate the positions of the protein molecular weight markers.

The present invention is based on identification of ECM-1, NP-I, H2A, and TIMP-2 as factors in lipogenesis. The invention was an outcome of differentiation studies with cultured human melanoma cell lines, including the SK-MEL-131 clone 3.44 (SKM) cell line (Thomson et al., 1988; Kiguchi et al., 1990a; Kiguchi et al., 1990b; Spieholz et al., 1995). Unexpectedly, during these studies, it was observed that medium from the SKM cultures had an ability to evoke the formation of massive lipid droplets in different cell types. This ability was observed by the inventors among other cells including human breast tumor cells described by Bacus et al., 1990; Giometti et al., 1995, melanoma cells described by Kiguchi, et al., 1990a; Kiguchi et al., 1990b, and leukemia cells described by Ryffel et al., 1982; Constantinou, 1990 as well as in the mouse 3T3 cells described by Green and Kehinde, 1974. For this reason, medium from these SKM cultures, namely SKM conditioned-medium (CM), was used as a source for the isolation and characterization of the lipogenins described in the present invention.

Protein Purification

To achieve standardization during lipogenin purification, the induction of lipid droplet formation by either the CM or materials from this medium was determined in the human AU-565 cells (same as the SKBr cells, American Type Culture Collection, Rockville, Md.) after staining with Oil Red. For this staining, exponentially growing AU-565 cells (Bacus et al., 1990) were inoculated into Lab-Tec four chamber-slides (Nunc Inc., Naperville, Ill.) at 0.5–1×104 cells/ml of medium per chamber. A modified "Oil Red O in propylene glycol" method was used to visualize neutral lipids (Sheehan, 1980) as previously described (Bacus et al., 1990). In short, after the medium was removed and the plastic component was detached, the Lab-Tec slides were rinsed with 0.05M phosphate buffered saline, pH 7.6, and the cells were fixed by a quick dip in −20° C. methanol/acetone (v/v). After fixation, the slides were placed in absolute propylene glycol for 2 min. at room temperature (22° C.) and then for 7 min. at room temperature in an Oil Red staining solution (Sigma Chemical Co. St. Louis, Mo.). The slides were then dipped into 85% isopropanol, rinsed with deionized water, counter-stained in Mayer's hemotoxylin (Sigma), blued in saturated lithium carbonate, and covered with glycerol jelly and a coverslip. One unit of lipogenic activity (ULA) was defined as the ability of the CM or materials from this medium to evoke a two-fold increase over the control in the number of lipid droplets. The increase in the number of lipid droplets was usually associated with an increase in their size. To facilitate lipogenin purification by eliminating the requirement for serum, which has an abundance of known and unknown proteins and peptides, the SKM cells were adapted to grow in a defined culture medium at 37° in a humidified atmosphere of 5% carbon dioxide. This medium consisted of RPMI-1640 plus 2 mM glutamin, 0.04% albumin from bovine serum, 0.001% transferrin, 0.001% insulin, 100 units/ml penicillin and 0.01% streptomycin (GIBCO, Grand Island, N.Y.). CM with this defined culture medium was collected from 150 mm tissue culture dishes (25–30 ml medium/dish), inoculated 6–10 days earlier with 104–105 SKM cells/ml. of medium. Even though the total lipogenic activity of this CM was lower than that of CM from serum-supplemented medium, its specific activity (ULA/U. V. absorbance at 280 nm, U/A) was about 20 fold higher than that of the serum-supplemented medium. Prior to its use in the subsequent purification procedures, the CM was centrifuged at 3,000×g to remove floating cells and cell debris.

Initially, 10 liter of the CM from the SKM cultured in the defined medium were stirred for 12 hours at 4° C. with 500 ml of heparin agarose resin (Amersham Pharmacia Biotech Comp, Piscataway, N.J.), which was earlier equilibrated with a solution of 50 mM Tris-HCL buffer (pH7.5), 0.01% ethylenediaminetetraacetic acid and a protease cocktail, composed of 4-(2 aminoethyl)benzenesulfonyl fluoride, pepstatin A, trans-epoxysuccinyl-L-leucyl-amido(4-guanidino)butane, bestatin, leupeptinand and aprotinin (Sigma, St. Louis, Mo.). After allowing the heparin resin to settle in a column, it was washed with 10 volumes of 50 mM Tris-HCL buffer solution (pH7.5). The heparin absorbed proteins were eluted once at 0. 5M NaCl and then at 2.5M NaCl. The 0.5M NaCl eluent, which contained about half of the total activity of the CM, had a specific activity of 180 U/A (Table 1).

Next, for size exclusion chromatography, the 0.5M NaCl eluent was concentrated and applied onto a Superdex 200 column (0.5×5 cm) (Amersham Pharmacia Biotech Comp.) in a solution of 50 mM Tris-HCL buffer (pH7.5) plus 0.15M NaCl and eluted at a flow rate of 0.5 ml/min. Under these conditions, the lipogenic activity was eluted at the void volume of the column, pointing out that the active material(s) was most likely a substance(s) with a molecular weight(s) of over 800 kDa (FIG. 1). To eliminate potential protein-protein interaction, the eluted void volume fraction was concentrated and applied again to the Superdex 200 column and eluted as before with one exception that the column was equilibrated and eluted in the presence of 4M urea. In this case, lipogenic activity was eluted in two separate fractions corresponding to molecular weights of about 60 Kda (fraction I) and 25 kDa (fraction II) (FIG. 1). Next, each of these fractions was dialyzed with a solution of 25 mM Tris-HCL buffer (pH7.5) containing 4M urea and applied for anion exchange chromatography onto a Mono Q column (0.5×5 cm) (Amersham Pharmacia Biotech Comp.), which was previously equilibrated with the above solution. The absorbed proteins were eluted by means of a 0–1M NaCl gradient in a solution of 25 mM Tris-HCL buffer (pH7.5) containing 4M urea. Under these conditions, the active portion of fraction I, which eluted at 50 mM NaCl, had a specific activity of about 1800 A/U, while the active portion of fraction II, which was eluted at 150 mM NaCl, exhibited a specific activity of about 900 A/U (Table 1). Final purification of the active portion from fraction I was achieved by cation exchange chromatography with Mono S column (Amersham Pharmacia Biotech Comp.). After dialysis with a solution of 25 mM NaAc buffer (pH 5.5) and 4M urea, the active portion of fraction I was applied to the Mono S column (0.5×5 cm) and eluted by means of a 0–1M NaCl gradient in the same solution at a flow rate of 0.5 ml/min. The lipogenin activity was eluted as single peak at 0.25M NaCl with a specific activity of more than 9000 A/U (Table 1). The material from this peak, after sodium dodecyl sulfate polyacrylamide-gel-electrophoresis (SDS-PAGE) under either reduced or non-reduced conditions, exhibited a single band with a molecular weight of about 50 kDa. This 50 kDa SDS-PAGE band was submitted for identification to a commercial laboratory, the W. M. Keck Foundation, Biotechnology Resource Laboratory at Yale University (New Haven, Conn.), the "Keck facility."

Initially, based on matrix assisted laser desorption ionization mass spectroscopy (MALDI-MS) of a portion of the digested bands and the subsequent seach by "ProFoud", a Rockefeller University (New York, N.Y.) computer program, which enables identification of a protein by comparing its peptide map to that in the National Center for Biotechnology data base, it was determined that ECM-1 may be present in this fraction, because ⅔ of the necessary criteria for unambiguous protein identification were met. Corroborating results were achieved after N-terminal sequencing of a peptide obtained by tryptic digest of the tested material. This sequencing yielded the following 10 amino acid residues; Asn-Leu-Pro-Ala-Thr-Asp-Pro-Leu-Gln-Arg, (portion of SEQ ID NO: 13) which matches position 324–333 of ECM-1. Besides, there is in ECM-1 a tryptic cleavage site prior to the first residue of this peptide, which would generate this peptide after ECM-1 trypsin digestion. Furthermore, the calculated mass of this peptide (1125.3 Da) was in agreement with the MALDI-MS data (1126.4 Da). However, there are two different ECM-1 transcripts (Smits et al., 1997). The larger one, ECM-1, codes for a protein of 540 amino acid residues with a calculated mass of 69.4 kDa, which is higher than that estimated by SDS-PAGE. The smaller transcript ECM-1 codes a protein of 415 amino acid residues with a calculated mass of 46.1. In addition, this transcript has two N-glycosylation sites and six phosphorylation sites, that would yield a mass around 50 kDa, which is similar to the SDS-PAGE estimate. In view of these observations, the lipogenic protein in fraction I is identified as the smaller ECM-1 transcript.

To achieve final purification of the active portion of fraction II, derived from the Mono Q column, hydrophobic chromatography was performed using a Phenyl Sepharose column (Amersham Pharmacia Biotech Comp.). Initially, this active portion was dialyzed with a solution of 50 mM Na-phosphate buffer (pH 7.5) and 2M ammonium sulfate and applied onto the Phenyl Sepharose column (0.5×5 cm), which was previously equilibrated with the same solution. Protein elution was performed using a 2–0M ammonium sulfate decreasing gradient at a flow of 0.5 ml/min. A single lipogenic fraction was obtained at 0.2M ammonium sulfate. At non-reducing or reducing conditions, this eluent yielded a single protein band on SDS-PAGE with a molecular weight of about 25 kDa. This eluent was submitted to the Keck facility for identification. After digestion, MALDI-MS and ProFound search, the eluent was determined to contain TIMP-2 (Stetler-Stevenson et al., 1989).

Figure 2:
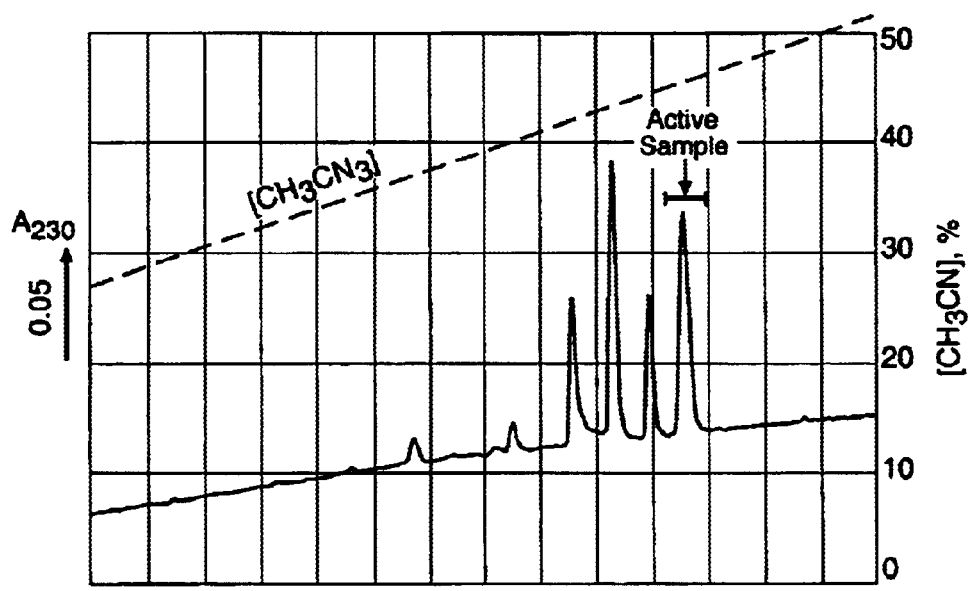
FIG. 2 shows cation-exchange chromatography of sample number III on Mono S column; an arrow indicates the position of the active sample; horizontal bars represent the sum of collected formations tested for activity.

The 2.5M NaCl heparin eluent contained about one sixth of the total lipogenic activity of the CM and a specific activity of about 90 A/U (Table 2). This eluent was diluted 5-fold with water and applied once more onto a heparin agarose resin column (0.5×5 cm), which was previously equilibrated with a solution of 50 mM Tris-HCL buffer (pH7.5) plus 0.5M NaCl. The heparin absorbed proteins were eluted with a 0.5–2.0M NaCl increasing gradient in a solution of 50 mM Tris-HCL buffer (pH7.5). Lipogenic activity was eluted at 0.8M (fraction III) and 1.25M NaCl (fraction IV), with specific activities of about 1200 and 400 A/U, respectively (Table 2). Final purification of fraction III was achieved by means of cation exchange chromatography with Mono S column (Amersham Pharmacia Biotech Comp.). After it was dialysed with a solution of 25 mM NaAc buffer (pH 5.5), fraction III was applied to Mono S column (0.5×5 cm). The proteins were eluted by means of a 0–1M NaCl increasing gradient at a flow rate of 0.5 ml/min in a solution of 25 mM sodium acetate buffer (pH 5.5). Lipogenic activity was eluted at 0.4M NaCl; this material yielded a specific activity of about 7000 A/U (FIG. 2). Under reduced conditions, the SDS-PAGE analysis of this material revealed a single band of about 50 kDa. After tryptic digestion of the protein in this band, MALDI-MS and ProFound search by the Keck facility, it was determined to contain NP-I (Sommer et al., 1987).

Figure 3:
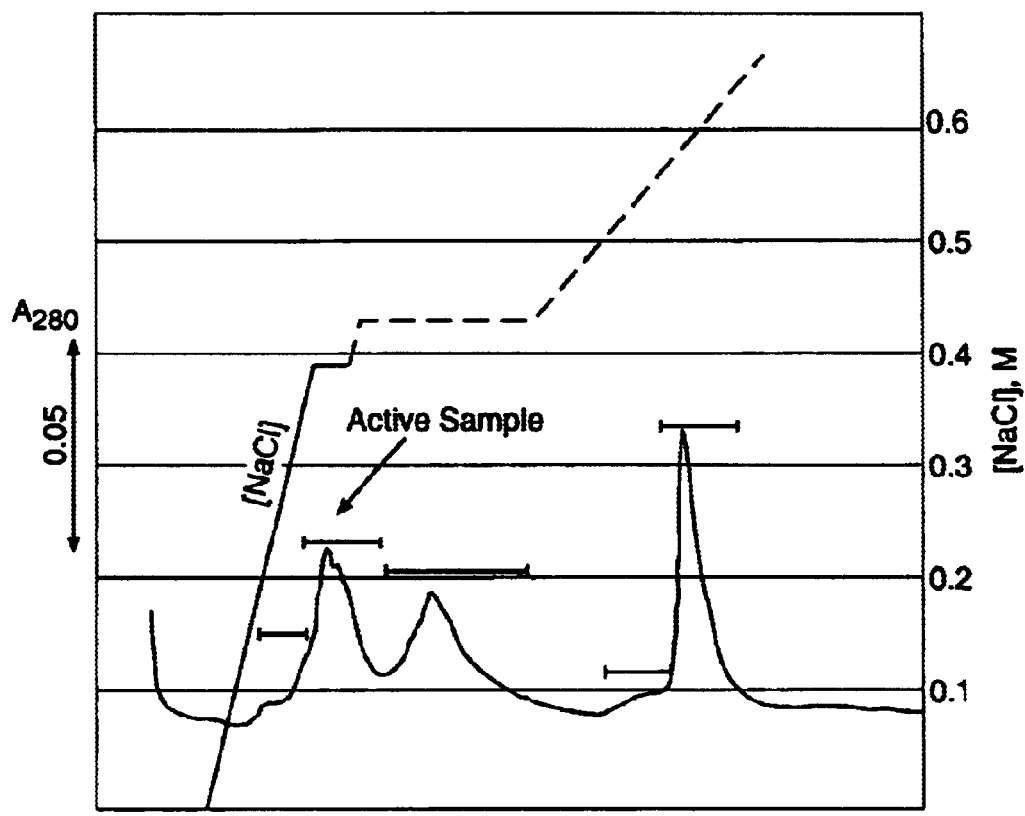
FIG. 3 shows reversed-phase chromatography of sample IV on a Nucleosyl C-4 column; see chromatographic conditions disclosed herein; an arrow indicates the position of the active sample; horizontal bars represent the sum of collected fractions tested for activity.

The final characterization of the active material in fraction IV was obtained by means of reversed phase chromatography with a Nucleosyl C-4 column. To achieve this characterization, fraction IV was injected into Nucleosyl C-4 column (0.4–15 cm), which was previously equilibrated 0.1% trifluoroacetic acid. The proteins were eluted with an increasing gradient of 0–80% acetonitryl, at a flow rate of 1 ml/min. The lipogenic activity was eluted as a sharp peak at 43% acetonitryl (FIG. 3), with specific activity of about 1800 A/U (Table 2). The material in this peak after SDS-PAGE under reduced conditions exhibited a single protein band of about 18 kDa. After tryptic digestion of the material in this peak, MALDI-MS and ProFound search by the Keck facility, it was determined to contain H2A.

The "active fraction" refers to proteins or peptides that induce droplet formation in cultured cells.

Identification of Proteins/Peptides That Bind to Lipogenins

The two-hybrid system (Field and Song, 1999) will be used to identify proteins or peptides to which ECM-1, NP-I, TIMP-2 or H2A bind, in order to achieve lipogenesis. The two-hybrid system will be performed as described in the "Matchmaker Gal4 two-hybrid system 3 and libraries user manual" by Clontech, Palo Alto, Calif. For example, to identify ECM-1, NP-I, TIMP-2 or H2A binding proteins, the coding region of their cDNA will be used as the bait. The entire coding region of ECM-1, NP-I, TIMP-2 or H2A cDNA and about 300 bp of their 3'-end untranslated region (UTR), obtained as a NcoI/EcoRI restriction fragment, will be directionally cloned into the NcoI/EcoRI site of pAST-1. This cloning should create a GAL4BD-ECM-1, NP-I, TIMP-2 or H2A reading frame fusion. Each of these fused plasmids will be transfected into S. cerevisiae strain AH109. This strain, which contains multiple reporter genes linked to distinct GAL4 upstream activation sequence (UAS), has been reported to reduce false positives due to promiscuous interaction of a prey protein by itself with an individual UAS (James et al., 1996).

To ensure that the full length GAL4BD-ECM-1, NP-I, TIMP-2 or H2A proteins will be synthesized, lysates from vector derived trp+ transformants will be obtained by lyticase/sodium dedocyl sulfate (SDS) treatment and analyzed by Western blotting using commercially obtained polyclonal-antibodies to each of these proteins. The GAL4BD-ECM-1, -NP-I, -TIMP-2 or -H2A transformants will be plated onto either -trp, -trp -ade, or -trp, -his dropout plates. To reduce background from leaky host HIS3 mutant, these plates also contain 2.5–15 mM 3-amin-1,2,4-triazole (3-AT), which is a competitive inhibitor of the yeast HIS3 protein (Durfee et al., 1993). To insure that the GAL4BD-ECM-1, -NP-I, -TIMP-2 or -H2A construct will not activate GAL4-dependent HIS3, MELI1, ADE2 or (beta-galactosidase) lacZ expression, the yeast will be assayed for either auxotrophy or growth as white colonies on X-alfa-gal plates (MELI), or lacZ filter assays. Suppression of background HIS3 will be achieved with 2.5 mM 3-AT. As a positive control, the strain will be transformed with the pCL1 plasmid, which encodes the full length of the GAL4 protein. The source of prey proteins will be commercial (Clontech) GAL4AD-cDNA libraries derived from human normal or tumor breast cells or from leukocytes or leukemia cells, because these cells are susceptible to the lipogenic effect of effect of ECM-1, NP-I, TIMP-2 or H2A.

The verification that these ECM-1, NP-I, TIMP-2 or H2A binding proteins or peptides are required for lipogenesis will be achieved by demonstrating that antisense cDNA or antisense oligonucleotides to these proteins or peptides, or neutralizing antibodies will be able to offset the lipogenic effect of ECM-1, NP-I, TINP-2 or H2A.

The antisense cDNA or antisense oligonucleotides will be based on the cDNA sequences encoding these proteins while the neutralizing antibodies will be either monoclonal or polyclonal antibodies made against these proteins or peptides by methods known to those of skill in the art.

Obtaining Recombinant Gene Products

Recombinant form of the ECM-1, NP-I, TIMP-2 or H2A or a portion thereof or their binding proteins or a portion thereof will be obtained through the use of a recombinant vector which incorporates the desired coding sequences (e.g. cDNA) together with its associated control (regulatory) sequences. Those skillful in the art have experience in the construction and preparation of such recombinant vectors (Sambrook et al., 1989; Ausubel et al.; U.S. Pat. No. 6,103,496). Similar expression vectors have to contain the DNA coding sequences to be expressed, in the case of this invention those encoding ECM-1, NP-I, TIMP-2 or H2A or a portion thereof or their binding proteins or a portion thereof. These coding sequences have to be positioned adjacent to and under the control of a promoter. To bring a coding sequence under the control of such a promoter, one commonly positions the 5' end of the transcription initiation site (of the transcriptional reading frame of the gene product to be expressed) between about 1 to 50 nucleotides downstream of the (3' end) chosen promoter. It is also desired to incorporate a polyadenylation site (e.g., 5'-AATAAA-3') into the transcriptional unit of the vector, if it is not already contained within the original inserted DNA. Typically, these sites are placed about 30 to 2000 nucleotides downstream of the coding sequence at a position prior to transcription termination. Although there is a preference for the use of the control sequences of the specific gene, there is no reason why other control sequences could not be employed, inasmuch as they are compatible with the genotype of the cell being targeted.

A promoter is a region of a DNA molecule typically within about 100 nucleotide pairs in front of (upstream of) the point at which transcription begins (i.e., a transcription start site). This region typically contains several types of DNA sequence elements, which usually are located in similar relative positions in different genes. Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also known in the art, the precise orientation and location of a promoter-enhancer relative to the coding sequence whose transcription is controlled, is dependent upon the specific nature of the enhancer-promoter. Thus, a TATA box minimal promoter is typically located from about 25 to about 30 base pairs upstream of a transcription initiation site and an upstream promoter element is,typically located from about 100 to about 200 base pairs upstream of a transcription initiation site. In contrast, an enhancer can be located downstream from the initiation site and can be at a considerable distance from that site. An enhancer-promoter used in a vector construct of the present invention can be any enhancer-promoter that drives expression in a cell to be transfected. By employing an enhancer-promoter with well-known properties, the level and pattern of gene product expression can be optimized.

For the introduction and expression of the sequences that codes for ECM-1, NP-I, TIMP-2 or H2A or a portion thereof or their binding proteins or a portion thereof, it is proposed to employ a vector construct that will deliver to the host the desired coding and control sequences, which are compatible with the host cell. Such vector/host systems can include, but not be limited to, microorganism such as bacteria transformed with a bacteriophage, plasmid, or cosmid expression vectors; yeast cells with a yeast expression vectors; insects cell systems with a baculovirus expression vector; plant cell systems with a cauliflower mosaic or tobacco virus expression vector, or with a bacterial expression vectors (e.g. pBR322 plasmid); and mammalian cells with a an appropriate mammalian expresion systems. The mammalian expression systems commonly use viral promoters derived from polyoma, cytomegalovirus (CMV), adenovirus (adeno), or simian Virus 40 (SV40).

The early and late promoters of SV40 virus are particularly useful because both are obtained easily from the virus as a fragment, which also contains the SV40 viral origin of replication. Smaller or larger SV40 fragments may also be used, provided there is included the approximately 250 base pair sequence extending from the Hind III site toward the Bgl I site located in the viral origin of replication. The origin of replication may be provided either by construction of the vector to include an exogenous origin, such as may be derived from SV40 or other viral (e.g., Polyoma, Adeno, CMV) source, or may be provided by the host cell chromosomal replication mechanism. If the vector is integrated into the host cell chromosome, the latter is often sufficient. Such vectors are preferred because they have been successfully used to deliver desired sequences to host cells and tend to have a high infection efficiency.

Production of Transgenic Non-human Animals

It is also contemplated to be within the scope of the present invention to prepare a transgenic non-human animal, which expresses the genes coding for ECM-1, NP-I, TIMP-2 or H2A or a portion thehereof or their binding proteins or a portion thereof. Techniques for the preparation of transgenic animals are known in the art (U.S. Pat. Nos. 5,489,742; 4,736,866; 5,550,316; 5,614,396; 5,625,125; 5,648,061; 573,933; 5,162,215 and 5,741,957, the entire contents of each of which are herein incorporated by reference).

With respect to an exemplary method for the preparation of a transgenic mouse, cloned recombinant or synthetic DNA sequences or DNA segments encoding ECM-1, NP-I, TIMP-2 or H2A or a portion thereof or their binding proteins or a portion thereof are injected into fertilized mouse eggs. The injected eggs are implanted in pseudo pregnant females and are grown to term to provide transgenic mice whose cells manifest ECM-1, NP-I, TIMP-2 or H2A or a portion thereof or their binding proteins or a portion thereof. The injected sequences are constructed having promoter sequences connected so as to express the desired protein in the all or a desired tissue of the transgenic mouse.

Purification of Recombinant Proteins

Purification of recombinant ECM-1, NP-I, TIMP-2 or H2A will be achieved using the procedure used for the purification of the natural form these proteins as described herein from cell lines. A simpler approach to purify these recombinant proteins or a portion thereof can involve the use of different types of affinity columns and high-performance liquid chromatography. Those skilled in the art have experience in the use of such methods (Janis and Regnier, 1988; Boyer and Hsu, 1993; and references therein). One can also construct an expression system in which the desired protein or peptide contains a tag (label) that will allow its isolation from a mixture of proteins and peptides derived from the host and growth medium. An example of such an approach is the FLAG-TAG system (Sigma) (Knappik and Pluckthun, 1994). The effectiveness of this system is due to the relatively small tag and the likelihood that the Flag sequence will fold at an exposed area of the protein. For example, in this approach, the coding region of ECM-1, NP-I, TIMP-2 or H2A or a portion thereof or their binding proteins or a portion thereof will be amplified by the polymerase chain reaction (PCR) using a high fidelity proofreading polymerase (Pfu, Srategene). Suitable primers include a 5'-Not I site and a 3'-Bam HI, which will be included in the final PCR product. This product will then be digested by Not I and Bam HI and directionally cloned into the Not I and Bam HI sites of the 2 amino-terminal of the FLAG expression vectors. pFLAG-CMV-1 incorporates a preprotrypsin leader sequence and the FLAG epitope into the expressed protein leading to its cellular excretion and leader sequence cleavage, whereas pFLAG-CMV-2 is designed for intercellular expression of the protein. Constructs obtained in each of these vector systems may be independently introduced into COS7B cells by electroporation and transient gene expression assayed 48h later. The presence of the pFLAG-CMV-1 in a complex with ECM-1, -NP-I, -TIMP-2 or -H2A or their binding proteins or a portion thereof will be monitored in conditioned medium from the transfected cells after SDS-PAGE by means of Western blotting and anti-FLAG antibody (FLAG, M2, Sigma). Expression of these proteins or peptides can also be monitored by direct cell immunostaining of formaldehyde fixed and lysophosphatidyl choline permeabilized cells with anti-FLAG antibody and goat anti-mouse-FITC. Such analyses can indicate expression of a FLAG tagged protein. Because of the much simpler nature of protein purification from condition medium in comparison of whole cell lysates, it is desirable to use the secreted form of the recombinant ECM-1, NP-I, TIMP-2 or H2A or their binding proteins or a portion thereof. After a large amount of condition medium is collected, from tissue culture dishes plates, the recombinant protein or peptide can be isolated by column-chromatography using ANTI-FLAG M2 affinity gel. Bound protein can be eluted with a solution of 0.1M glycine, pH 3.5, and the collected fractions pooled and concentrated. SDS-PAGE electrophoresis followed by protein staining should reveal the presence of the desired single protein band with the appropriate molecular weight.

Production of Antibodies

Antibodies can be raised to an antigen, which in this invention is defined as either the natural occurring form or recombinant form of ECM-1, NP-I, TIMP-2 or H2A or a portion thereof or to their binding proteins or a portion thereof. Additionally, antibodies can be raised to the native or denatured version of these proteins or peptides. A patent teaching the preparation of such antibodies is U.S. Pat. No. 6,111,090. The antibodies, including binding fragments and single chain fragments, against the antigen, a predetermined fragment of the antigen or such an antigen conjugated with an immunogenic molecule can be raised by immunization of animals. Monoclonal antibodies are prepared from cells secreting the desired antibody. These antibodies can be screened for binding to the antigen or for an agonistic or antagonistic activity e.g., by sterically blocking the ligand binding to its binding partner.

The antibodies in this invention can also be used in diagnostic applications. As capture or non-neutralizing antibodies, they can be screened for their ability to bind to the antigens without inhibiting biding by a partner. As neutralizing antibodies, they can be useful in competitive binding assays. They will also be useful in detecting or quantifying the natural occurring form or recombinant form of ECM-1, NP-I, TIMP-2 or H2A or a portion thereof or to their binding proteins or a portion thereof [e.g. Chan (ed) (1987); Price and Newman (eds) (1991); and Ngo (ed) (1988)]. Cross absorption or other tests will identify antibodies which exhibit various spectra of specificities, e. g., unique or shared species specificities. Further, the antibodies, including antigen-binding fragments, of this invention can be potent antagonists that bind to the antigen and inhibit functional binding or inhibit the ability of a binding partner to elicit the lipogenic response. They can also be useful as non-neutralizing antibodies and can be coupled to toxins or radionuclides so that when the antibody binds to the antigen, a cell expressing it, e.g., on its surface, is killed. Further, these antibodies can be conjugated to drugs or other therapeutic agents, either directly or indirectly by means of a linker, and may effect drug targeting.

In some instances, it is desirable to prepare monoclonal antibodies from various mammalian hosts, including rodents (e.g. mice) and primates (e.g. humans) (Stites, et al. (eds), Harlow and Lane, 1988; Goding, 1986; and Koler and Milstein, 1975).

Other suitable techniques involve in vitro exposure of lymphocytes to the antigens or alternatively to selection of libraries of antibodies in phage or similar vecrors (Huse et al., 1989; and Ward et al., 1989). In addition, one can produce recombinant immunoglobulins (U.S. Pat. Nos. 4,816,567 and 4,642,334; Queen et al., 1989).

The antibodies of the present invention may be used with or without modification, including chimeric or humanized antibodies. Frequently the antibodies or the antigen will be labeled by joining, either covalently or non-covalently, a substance which provides for a detectable signal. A wide variety of labels and conjugation techniques are known and are reported extensively in both scientific and patent literature. Suitable labels include radionuclides, enzyme, substrates, cofactors, inhibitors, fluorescence moieties, magnetic particles and the like (U.S. Pat. Nos. 3,817,837; 3,850,752; 3,939,350; 3,996,345; 4,277,437; 4,275,149; and 4,366,241).

The antibodies of this invention can also be used for affinity chromatography in isolating the natural occurring form or recombinant form of ECM-1, NP-I, TIMP-2 or H2A or a portion thereof or to their binding proteins or a portion thereof (Wilchek et al., 1984).

Antibodies against the natural occurring form or recombinant form of ECM-1, NP-I, TIMP-2 or H2A or a portion thereof or to their binding proteins or a portion thereof can also be used to raise anti-idiotipic antibodies, which will be useful in detecting or diagnosing obesity.

Antisense Methodology

Antisense methodology takes advantage of the fact, that DNA or RNA pair with complementary sequences according to the standard Watson-Crick rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Both RNA and DNA antisense sequences can be used to modify gene expression. These nucleic acids can be introduced into target cells directly or by means of a carrier device (e.g. liposomes) or by creation of an expression vector that transcribes the desired antisense sequence in the transfected cells. Targeting double-stranded DNA with complementary polynucleotides leads to triple-helix formation; targeting RNA will lead to double-helix formation.

Antisense polynucleotides, when introduced into a target cell, specifically bind to their target region in the nucleic acid and interfere with transcription, RNA processing, RNA transport, translation and/or stability. Antisense constructs may be employed to inhibit gene transcription or translation or both within a host cell, either in vitro or in vivo, such as within a host animal, including a human subject (Lonnberg and Vuorio, 1996; Bennett, 1998; Varga et al., 1999; Stein, 2000).

Antisense constructs may be designed to bind to the promoter and other control regions, exons, introns or even exon-intron boundaries of a gene. A way to verify that the designed antisense RNA and/or DNA is functioning as desired, can be achieved by in vitro testing the construct for its ability to modify the expression of the targeted gene. As stated above, antisense usually will mean nucleic acid sequences that are substantially complementary over their entire length and have very few base mismatches. For example, sequences of fifteen bases in length may be termed complementary when they have complementary nucleotides at thirteen or fourteen positions. Other sequences with lower degrees of homology also are contemplated. For example, an antisense construct can be designed which has regions of high homology as well as non-homologous regions (e.g., ribozyme). Although having less than 50% homology, these molecules may bind to target sequences under specific conditions.

As previously done in another system (Semizarov et al., 1998), the following is an example for the use of antisense oligonucleotides in the modulation of the expression of a gene that codes for the ECM-1, NP-I, TIMP-2 or H2A binding protein, which may result in inhibition of lipogenesis induced in AU-525 or other appropriate human or mammalian cells by the relevant lipogenin. Based on the analysis of the secondary structure of the gene's MRNA, which can be predicted by means of the FOLDRNA program (Zuker, M., 1989: Mathews et al., 1999), the antisense oligonucleotides can be directed against predicted single stranded structures located near the translation start codon. One can use antisense pentadecamers, because this length is sufficient for theoretical uniqueness within the human or other mammalian genomes. At the same time, such pentadecamers are short enough to ensure strong binding to single-stranded regions of the mRNA and exhibit adequate binding to regions that have some secondary or tertiary structure limitations (Wickstrom et al., 1988). In addition to the use antisense pentadecamers, one needs to use the corresponding sense pentadecamers as controls. To retard the degradation of the pentadecamers, the target cells will be pelleted and resuspended in serum-free culture medium containing 2–50 uM of a pentadecamer and incubated for up to 12 h. Bovine fetal serum will then be added together with the appropriate lipogenin inducer. One to four hours later, a fraction of the cells will be tested by means of Western blotting to determine the expression level of the tested gene, while another fraction will be tested after 1–3 days of incubation to determine lipid droplet production and/or manifestation of other adipogenic markers.

Another example may involve the construction of an antisense vector, which may be used to inhibit the expression of a gene that codes for an ECM-1, NP-I, TIMP-2 or H2A binding protein (Iznat and Weintraub, 1985; Semizarov et al., 1998). Among others, such a construct can involve a tetracycline-responsive expression vector, which expresses either the 5'-untranslated region (UTR) of the desired cDNA or its entire coding region as a sense or an antisense RNA. These vectors can be used in either a transient or stable transfection of cells. The efficacy of such a construct can be tested after transfection by dteremining the expression of the target gene by Western blotting and induction of lipogenesis by lipid droplet production and/or other adipogenic markers.

In a specific example for the vector construction, the 5'-UTR of the cDNA that codes for an ECM-1, NP-I, TIMP-2 or H2A binding protein will be isolated as Sal I-Nco I fragment of the cDNA. This fragment will be rendered blunt-ended with Pfu polymerase and ligated into the tetracycline responsive CMV plasmid pTRE (Clontech) in its blunted Eco RI site. Plasmids expressing the cDNA's 5'-UTR in the sense and antisense will be produced. To create a plasmid expressing the cDNA as an antisense RNA, the Bam HI-Sal I fragment containing the coding region and 5'-UTR will be isolated, blunted, and cloned into the blunted Eco RI site of pTRE.

For transient transfection analyses, cells will be concentrated by centrifugation, washed twice in PBS, and resuspended in PBS at $2.5 \ 10^7$ cells/ml. Plasmids will be sterilized by ethanol precipitation and resuspended in PBS. For each transfection, 2–20 µg of each plasmid in 200 µl PBS will be mixed with 200 µl of the cell suspension in a 0.2 cm electroporation cuvette, and allowed to equilibrate for 10 min on ice. DNA concentrations will be maintained equivalent between transfections by the addition of inert carrier plasmid. Electroporation will be then performed by using a T820 ElecroSquarePorator square-wave electroporation device (BTX, San Diego) delivering two pulses of 500 V for 99 µsec/pulse. Cells will then be diluted with 4 ml of ice-cold culture medium and incubated on ice for 10 min before plating.

After 18 h of recovery, ECM-1, NP-I, TIMP-2 or H2A and/or tetracycline (10 µg/ml) will be added to the cells, which will be tested for the inhibition of the appropriate gene expression and manifestation of lipogenesis. For stable transfections, the above vector will also include a gene that bestows a selective advantage for the transfectants in a mixed cell population. An example for such a gene, is the bacterial neomycin phosphotransferase (neo) gene that confers resistance to the antibiotic G418 (Geneticin, Sigma). After the recovery the cells are incubated with culture medium containing G418, which allows the outgrowth of cells that maintain the vector with the neo gene into colonies (Tonetti et al., 1994). These colonies are then isolated and their cells cultured in the presence and absence of the ECM-1, NP-I, TIMP-2 or H2A and/or tetracycline to determine for the inhibition of the appropriate gene expression and manifestation of lipogenesis.

Candidate Inhibitor Assays and Kits

U.S. Pat. No. 6,110,723 (Powell) teach a means whereby ECM-1, NP-I, TIMP-2 or H2A or a portion thereof, or their binding proteins and peptides or a portion thereof or recombinant ECM-1, NP-I, TIMP-2 or H2A and their binding proteins or peptides or a portion thereof, or the nucleic acids that code for these proteins or peptides can be used to identify chemicals that will inhibit or mimic the activity of these macromolecules in human and other mammalian cells. Whenever ECM-1, NP-I, TINP-2 or H2A or a portion thereof or their binding proteins or peptides or a portion thereof are mentioned, it should mean both the natural and recombinant form of these macromolecules. These protein and peptides and the nucleic acids macromolecules can be assayed for their interaction with the chemicals in, e.g., cells, cell-free preparations, chemical libraries, and natural product mixtures. These chemicals can be natural chemicals or may be structural or functional mimetics. (e.g., Coligan et al.,1991).

The natural or recombinant proteins, peptides and/or the nucleic acids that code for these proteins or peptides (PPNs) of the present invention are responsible for many biological functions, including lipogenesis, which can be critical for obesity, as herein before mentioned. It is therefore desirable to devise screening methods to identify compounds which stimulate or which inhibit the function of these PPN and thus may act as drugs for the control of obesity and related as well as other disorders. Accordingly, the present invention provides methods of screening compounds to identify those which stimulate or which inhibit the function of a PPN of the invention, as well as related PPNs.

The screening methods may simply measure the binding of a candidate compound to the PPN, or to cells or membranes bearing the PPN, or a fusion protein of the protein or peptide by means of a label directly or indirectly associated with the candidate compound. Alternatively, the screening method may involve competition with a labeled competitor. Further, these screening methods may test whether the candidate compound results in a signal generated by activation or inhibition of the PPN, using detection systems appropriate to the cells comprising the PPN. Inhibitors of activation are generally assayed in the presence of a known agonist, which in our case can be, but not limited to, ECM-1, NP-I, TIMP-2 or H2A or a portion thereof. The effect on activation by the agonist in the presence of the candidate compound is observed. Constitutively active protein or peptide and/or constitutively expressed PPN may be employed in screening methods for inverse agonists or inhibitors, in the absence of an agonist or inhibitor, by testing whether the candidate compound results in inhibition of activation of the PPN, as the case may be. The screen may also in vitro determine the inhibitory effect of the candidate compound on the interaction between ECM-1, NP-I, TIMP-2 or H2A or a portion thereof with their binding protein, peptide or a portion thereof.

The antibodies that bind to and/or interact with ECM-1, NP-I, TIMP-2 or H2A or a portion thereof or their binding proteins or peptides or a portion thereof can also be used in a screening assay. For example, an ELISA assay may be constructed for measuring secreted or cell associated levels of ECM-1, NP-I, TIMP-2 or H2A or a portion thereof using monoclonal and polyclonal antibodies by standard methods known in the art. This can be used to discover agents that may inhibit or enhance the production of these protein or peptides from suitably manipulated cells or tissues.

The invention also provides a method of screening compounds to identify those which enhance (agonist) or block (antagonist) the action of ECM-1, NP-I, TIMP-2 or H2A or a portion thereof or their binding proteins or peptides or a portion thereof, particularly those compounds involved in lipogenesis. The method of screening may involve high-throughput techniques. For example, to screen for agonists or antagonists one can use a synthetic reaction mix that may contain, but not be limited to, a cellular compartment, such as a membrane, cell envelope or cell wall, or a preparation of any thereof, and ECM-1, NP-I, TIMP-2 or H2A or a portion thereof and a labeled substrate, ligand or a binding protein or peptide of ECM-1, NP-I, TIMP-2 or H2A or a portion thereof in the absence or the presence of a candidate molecule that may be an agonist or antagonist. The ability of the candidate molecule to agonize or antagonize the ECM-1, NP-I, TIMP-2 or H2A or a portion thereof or their binding proteins or peptides or a portion thereof is reflected in decreased binding of the labeled ligand or decreased production of a product from such substrate. Molecules that bind gratuitously, i.e., without inducing the lipogenic effect of ECM-1, NP-I, TIMP-2 or H2A or a portion thereof are most likely to be good antagonists. Molecules that bind well and, as the case may be, increase the rate of product production from substrate, increase signal transduction, or increase chemical channel activity are agonists. The described assays may also involve reporter systems that are well known in the art, which may include but are not be limited to, colorimetric labeled substrate converted into a product or a reporter gene, that is responsive to changes in the activity or binding of ECM-1, NP-I, TIMP-2 or H2A or a portion thereof to their binding proteins or peptides or a portion thereof.

The ECM-1, NP-I, TIMP-2 or H2A or a portion thereof or their binding proteins or peptides or a portion thereof may be used to identify membrane bound or soluble receptors, if any, for such proteins and peptides, through standard receptor binding techniques known in the art. These techniques include, but are not limited to, ligand binding and crosslinking assays in which the protein or peptide or a portion thereof is labeled with a radioactive isotope (for instance, $^{125}$I), chemically modified (for instance, biotinylated), or fused to a peptide sequence suitable for detection or purification, and incubated with a source of the putative receptor (e.g., cells, cell membranes, cell supernatants, tissue extracts, bodily materials).

Other methods include biophysical techniques such as surface plasmon resonance and spectroscopy. These screening methods may also be used to identify agonists and antagonists of ECM-1, NP-I, TIMP-2 or H2A or a portion thereof binding to their receptor(s) or other binding proteins or peptides or a portion thereof, if any. Standard methods for conducting such assays are well understood in the art.

The fluorescence polarization value for a fluorescently-tagged molecule depends on the rotational correlation time or tumbling rate. Protein complexes, such as formed by ECM-1, NP-I, TIMP-2 or H2A or a portion thereof in association with their binding protein or peptides or a portion thereof, labeled to comprise a fluorescently-labeled molecule will have higher polarization values than a fluorescently labeled monomeric protein. It is preferred that this method be used to characterize small molecules that disrupt polypeptide complexes.

Fluorescence energy transfer may also be used identify molecules that interfere with the formation of a PPN of this invention. In addition, fluorescence energy transfer may be used to identify molecules that interfere with the binding of ECM-1, NP-I, TIMP-2 or H2A or a portion thereof with their binding proteins or peptides or a portion thereof. ECM-1, NP-I, TIMP-2 or H2A or a portion thereof or ECM-1, NP-I, TIMP-2 or H2A or a portion thereof binding proteins or peptides or a portion thereof can be labeled with both a donor and acceptor fluorophore. Upon mixing of the two-labeled species and excitation of the donor fluorophore, fluorescence energy transfer can be detected by observing fluorescence of the acceptor. Compounds that block dimerization will inhibit fluorescence energy transfer.

Surface plasmon resonance can be used to monitor the effect of molecules on the self-association as well as an association of ECM-1, NP-I, TIMP-2 or H2A or a portion thereof with their binding proteins or peptides or a portion thereof and another molecule. ECM-1, NP-I, TIMP-2 or H2A or a portion thereof or their binding proteins or peptides or a portion thereof can be coupled to a sensor chip at low site density such that covalently bound molecules will be monomeric.

A scintillation proximity assay may be used to characterize the binding between ECM-1, NP-I, TIMP-2 or H2A or a portion thereof with their binding proteins or peptides or a portion thereof as well as with other protein or peptide. In such a case ECM-1, NP-I, TIMP-2 or H2A or a portion thereof or their binding proteins or peptides or a portion thereof can be coupled to a scintillation-filled bead.

ICS biosensors have been described by AMBRI (Australian Membrane Biotechnology Research Institute). They couple the self-association of macromolecules to the closing of gramacidin-facilitated ion channels in suspended membrane bilayers and hence to a measurable change in the admittance (similar to impedance) of the biosensor. This approach is linear over six decades of admittance change and is ideally suited for large scale, high throughput screening of small molecule combinatorial libraries.

In other embodiments of the invention methods are provided for identifying compounds, which bind to or otherwise interact with and inhibit or activate an activity or expression of a PPN of this invention. These methods include as follows: a) contacting a PPN with a compound to be screened under conditions that permits binding to or other interaction between the compound and the PPN to assess the binding to or other interaction with the compound, such binding or interaction preferably being associated with a second component capable of providing a detectable signal in response to the binding or interaction of the PPN with the compound; and b) determining whether the compound binds to or otherwise interacts with and activates or inhibits an activity or expression of the PPN of this invention by detecting the presence or absence of a signal generated from the binding or interaction of the compound with the PPN. Another example of an assay for an agonist of ECM-1, NP-I, TIMP-2 or H2A or a portion thereof, is a competitive assay that combines ECM-1, NP-I, TIMP-2 or H2A or a portion thereof and a potential agonist with an ECM-1, NP-I, TIMP-2 or H2A binding protein or peptide or a portion thereof, natural substrates or ligands, or substrate or ligand mimetics, under appropriate conditions for a competitive inhibition assay. ECM-1, NP-I, TIMP-2 or H2A or a portion thereof or their binding proteins or peptides or a portion thereof can be labeled by radioactivity or a colorimetric compound, such that the ECM-1, NP-I, TIMP-2 or H2A or a portion thereof or their binding protein or peptide or a portion thereof interacts with a molecule that can be converted to a product that can be determined accurately, to assess the effectiveness of the potential antagonist.

Potential antagonists include, among others, small organic molecules, peptides, polypeptides and antibodies that bind to one or more of the PPNs of this invention and thereby inhibit or extinguish its activity or expression. Potential antagonists also may be small organic molecules, a peptide, a polypeptide such as a closely related protein or peptide, or antibody that binds the same sites on a binding molecule, such as a binding molecule, without inducing ECM-1, NP-I, TIMP-2 or H2A-evoked activities, thereby preventing the action or expression of the PPNs by excluding ECM-1, NP-I, TIMP-2 or H2A or a portion thereof from binding.

Potential antagonists include a small molecule that binds to and occupies the binding site of the protein or peptide thereby preventing binding to cellular binding molecules, such that normal biological activity is prevented. Examples of small molecules include but are not limited to small organic molecules, peptides or peptide-like molecules. Other potential antagonists include antisense molecules as previously described.

Other examples of potential protein or peptide antagonists include antibodies or, in some cases, proteins or peptides, which are closely related to ECM-1, NP-I, TIMP-2 or H2A or a portion thereof or their binding proteins or peptides or a portion thereof, or substrates, receptors, enzymes, etc., as the case may be, of ECM-1, NP-I, TIMP-2 or H2A or a portion thereof or their binding proteins or peptides or a portion thereof, e.g., a fragment of the ligands, substrates, receptors, enzymes, etc.; or small molecules which bind to ECM-1, NP-I, TIMP-2 or H2A or a portion thereof or their binding proteins or peptides but do not elicit a lipogenic response, so that the activity of the protein or peptide is prevented.

In another aspect, the present invention relates to a screening kit for identifying agonists, antagonists, ligands, receptors, substrates, enzymes, etc. of a PPN of the present invention, or compounds which decrease or enhance the production of such a PPN. Such a screening kit can comprise: (a) a PPN of the present invention; (b) a recombinant cell expressing a PPN of the present invention; (c) a cell membrane expressing a PPN of the present invention; or (d) antibody to a PPN of the present invention. It will be appreciated that in any such kit, (a), (b), (c) or (d) may comprise a substantial component.

Drug Design

It will be readily appreciated by the skilled artisan that ECM-1, NP-I, TIMP-2 or H2A or a portion thereof or their binding proteins or peptides or a portion thereof may also be used in structure-based design of an agonist, antagonist or an inhibitor of such a protein or peptide (Klebe, 2000; Smyth and Martin, 2000). The structure based design approach may involve (a) in the first instance, determining the three-dimensional structure of ECM-1, NP-I, TIMP-2 or H2A or a portion thereof or their binding proteins or peptides or a portion thereof or a complexes thereof; (b) deducing the three-dimensional structure for the likely reactive site(s), binding site(s) or motif(s) of an agonist, antagonist or inhibitor; (c) synthesizing candidate compounds that are predicted to bind to or react with the deduced binding site(s), reactive site(s), and/or motif(s); and (d) testing whether the candidate compounds are indeed agonists, antagonists or inhibitors.

It will be further appreciated that this will normally be an iterative process, and this iterative process may be performed using automated and computer-controlled steps.

Methods of Treating Lipid-related Conditions

In a further aspect, the present invention provides methods of treating abnormal conditions such as, for instance, a disease, obesity in particular, related to either an excess of, an under-expression of, an elevated activity of, or a decreased activity of ECM-1, NP-I, TIMP-2 or H2A or a portion thereof or their binding proteins or peptides or a portion thereof.

If the expression and/or activity of the PPN are in excess, several approaches are available. One approach may involve administering to an individual in need thereof an inhibitor compound (antagonist) as herein described, optionally in combination with a pharmaceutically acceptable carrier. The amount should be effective in inhibiting the function and/or expression of the PPN of this invention, such as, for example, by blocking the binding of ligands, substrates, receptors, enzymes, etc., or by inhibiting a second signal, and thereby alleviating the abnormal condition. In another approach, soluble forms of the PPN still capable of binding the ligand, substrate, enzymes, receptors, etc. in competition with an endogenous PPN may be administered. An examples of such competitors include ECM-1, NP-I, TIMP-2 or H2A or a portion thereof or a binding protein or peptide or a portion thereof, or antibodies to these proteins or peptides as well as antiidiotypes to these antibodies. Another example may involve the use of a genetically construct, which includes ECM-1, NP-I, TIMP-2 or H2A or a portion thereof or their binding proteins or peptides or a portion thereof fused with another molecule. Furthermore, this invention relates to processes for the preparation of Examples of fusion protein technology can be found in International Patent Application Nos. WO94/29458 and WO94/22914.

In still another approach, expression of the gene encoding endogenous ECM-1, NP-I, TIMP-2 or H2A or a portion thereof or their binding proteins or peptides or a portion thereof can be inhibited using expression-blocking techniques. This blocking may be targeted against any step in gene expression, but is preferably targeted against transcription and/or translation. An examples of a known technique of this sort involve the use of antisense sequences (as mentioned earlier), either internally generated or separately administered (O'Connor, 1991). Alternatively, oligonucleotides which form triple helices with the gene can be supplied (Lee et al., 1979; Cooney et al., 1988; Dervan et al., 1991). These oligomers can be administered per se or the relevant oligomers can be expressed in vivo.

TABLE 1

Purification of Adipogenic Factors From the Sample Eluted From Heparin by 0.5M NaCl

| Step | Volume, ml | Total Activity, ULA | Specific Activity, A/U | Purification Level | Yield % |
|---|---|---|---|---|---|
| 0. Conditioned medium | 10,000 | 8,800 | 0.9 | 1 | 100 |
| 1. Affinity Heparin gel (elution by 0.5M) | 100 | 4,490 | 180 | 200 | 51 |
| 2. Anion-exchange I MonoQ (4M urea):II | 1.5 2.6 | 1,320 700 | 1,760 890 | 1,960 990 | 15 8 |
| 3a. Cation-exchange Mono S (4M urea):I | 3 | 530 | 9,300 | 10,330 | 6 |
| 3b. Hydrophobic Phenyl-Speharose:II | 1 | 260 | 1,200 | 330 | 3 |

TABLE 2

Purification of Adipogenic Factors From the Sample Eluted from Heparin by 2.5M NaCl

| Step | Volume, ml | Total Activity, ULA | Specific Activity, A/U | Purification Level | Yield % |
|---|---|---|---|---|---|
| 0. Conditioned medium | 10,000 | 8,800 | 0.9 | 1 | 100 |
| 1. Affinity Heparin gel (elution by 2.5M NaCl) | 30 | 1,410 | 90 | 100 | 16 |
| 2. Heparin column: | | | | | |
| III | 1.5 | 530 | 1,170 | 1,300 | 6 |
| IV | 2.0 | 260 | 420 | 470 | |
| 3a. Cation-exchange Mono S (physiological):III | 0.5 | 350 | 7,040 | 7,820 | 4 |
| 3b. Hydrophobic Phenyl-Speharose: IV | 0.5 | 180 | 1,800 | 2,000 | 2 |

DOCUMENTS CITED

Ailhaud G., et al., Cellular and molecular aspects of adipose tissue development. Ann. Rev. Nutr., 12: 207–233, 1994.

Ailhaud G., et al., Hormonal regulation of adipose differentiation. Ann. Rev. Nutr., 12: 132–136, 1994.

Albig et al. (1997) Hum. Genet. 101(3): 284–294.

Allison, D. B. et. al. The heritability of body mass index among an international sample of monozygotic twins reared apart. Int. J. Obes. Relat. Metab. Disord., 20: 501–506, 1996.

Ausubel et al. Current Protocols in Molecular Biology, John Wiley & Sons, New York, N.Y.; U.S. Pat. No. 6,103, 496.

Bacus S. S. Kiguchi K., Chin D., King C. R., and Huberman E. Differentiation of cultured human breast cancer cells (Au-565 and MCF-7) associated with loss of cell surface HER/neu Antigen. Mol. Carcin., 3: 350–362, 1990.

Barch G. S. et. al. Genetics of body-weight regulation. Nature 404: 644–651, 2000.

Barerett A. J. In: Proteinase Inhibitors, Ed. Barrettt A. J., et al. Elsevier, Amsterdam, p. 3–22, 1986.

Bennett, C. F. Antisense oligonucleotides: is the glass half full or half empty? Biochem. Pharmacol. 55: 9–19, 1998.

Bhalerao J., Tylzanowski P., Filie J., Kozak C., and Merregaert J. J. Biol. Chem. 270: 16385–16394, 1995.

Bode W. et al. Insight into MMP-TIMP interactions. Ann. N Y Acad. Sci. 30: 73–91, 1999; Brew K. et al. Tissue inhibitors of metaloproteinases: evolution, structure and function. Biochem. Biophys. Acta 1477: 267–283, 2000.

Bouchard, C. et. al. The response to long-term overfeeding in identical twins. N. Eng. J. Med. 322:1477–1482, 1990.

Boyer, P. M. and Hsu, J. Protein purification by dye-ligand chromatography. Adv. Biochem. Eng. Biotechnol. 49:1–44, 1993.

Brown O. A. et al. Gonadotrophin-releasing activity of histone H2A and H2B. Cell Mol. Life Sci. 54: 288–294, 1998.

Brun R. P., et al., Adipocyte differentiation: a transcription regulatory cascade. Current Opinion in Cell biol. 6: 826–832, 1996.

Chan (ed) (1987) Immunology: A practical guide, Acadmic Press, Orlando, Fla.

Clement, K., et al. A mutation in human leptin receptor gene causes obesity and pituitary dysfunction, Nature, 392:398–401, 1997.

Coligan et al., Current Protocols in Immunology 1(2): Chapter 5 (1991).

Constantinou A. Induction of differentiation and DNA strand breakage in human HL-60 and K-562 leukemia cells by genistein. Cancer Res. 50:2618–2624, 1990.

Cooney et al., Science 241:456, 1988.

Cornelius P., et al., Regulation of adipocyte development. Ann. Rev. Nutr., 14: 99–129, 1994.

Dervan et al., Science 251:1360, 1991.

Diaz-nido J. et al. Addition of protease inhibitors to culture medium of neroblastoma cells induces both neurite out growth and phosphorylation of microtubule-associated protein MAB-1B. J. Cell Sci. 98:409–419, 1992.

Dobner et al. (1991) DNA Seq, 1(6):409–413.

Durfee T. et al. The retinoblastoma protein associates with the protein phosphatase type I catalytic subunit. Genes Dev. 7: 555–569, 1993.

Field S. and Song O. A novel genetic system to detect protein-protein interactions. Nature 340:245–246, 1989; Vidal M. and Lengrin P. Yeast forward and reverse 'n'-hybrid systems. Nucleic Acids Res.27: 919–929, 1999.

Gibbs J. B. Mechanism-based target identification and drug discovery in cancer research. Science 287: 1969–1973, 2000.

Giometti C. S., et al. Analysis of proteins from human breast epithelial cells using two-dimentional gel electophoresis. Elecrophoresis 16:1215–1224, 1995.

Goding (1986) Monoclonal antibodies: Principle and practice ($2^{nd}$ ed.), Academic Press, New York, N.Y.

Goldberg G. I. et al. Human 72-kilodalton type IV collagenase forms a complex with tissue inhibitor of metaloproteinase designated TIMP-2. Proc. Natl. Acad. Sci. USA. 86: 8207–8011, 1989.

Green H., and Kehinde, O. Sublines of 3T3 cells that accumulate lipid. Cell 1: 113–116, 1974.

Harlow and Lane (1988) Antibodies: A laboratory manual, CSH Press.

Hatch and Bonner (1988) Nuc. Acids Res. 16:1113–1124.

Hill, J. O. and Peters, J. C. Environmental contribution to the obesity epidemic. Science 280: 1371–1374, 1998.

Huse, et al. Generation of a large combinatorial library of the immunoglobulin repertoire in phage lanbda. Science 246: 1275–1281, 1989.

Iznat, J. G. and Weintraub, H. Constitutive and conditional suppression of exogenous genes by antisense RNA. Science 229: 345–352, 1985.

James P. et al. Genomic libraries and a host sreain designated for highly efficient two-hybrid selection in yeast. Genetics 144: 1425–1436, 1996.

Janis, L. J and Regnier, F. E. Immunological-chromatographic analysis. J. Chromatogr. 444: 1–11, 1988.

Kiguchi, K. et al. Induction of cell differentiation in melanoma cells by inhibitors of IMP dehydrogenase: Altered patterns IMP dehydrogenase expression and activity. Cell growth and differ. 1: 259–270, 1990.

Kiguchi, K. et al. Genistein-induced cell differentiation and protein-linked DNA strand breakage in human melanoma cells. Cancer Comm. 2:271–278, 1990.

Kiguchi K., et al. Differentiation of cultured human breast cancer cells (Au-565 and MCF-7) associated with loss of cell surface HER/neu Antigen. Mol. Carcin., 3: 350–362, 1990.

Klebe, G. Recent developments in structure-based drug design. J. Mol. Med. 78: 269–281, 2000.

Knappik, A. and Pluckthun, A. A novel affinity tag based on the FLAG peptide for the detection and purification of recombinant antibody fragments. Biotechniques 17: 754–761, 1994.

Koler and Milstein (1975) Nature 256: 495–497.

Kopelman, P. G., Nature 404: 635–643, 2000.

Lee et al., Nucleic Acids Res 6:3073, 1979.

Lonnberg, H. and Vuorio, E. Towards genomic drug therapy with antisense oligonucleotides. Ann. Med. 28: 511–522, 1996.

Mandrup S. and Lane D. M., Regulating adipogenesis. J. Biol. Chem. 272: 5367–5370, 1997.

Mannironi et al. (1989) Nuc. Acids Res. 17(22): 9113–9126.

Mannironi et al. (1994) DNA Cell Biol. 13(2): 161–170.

Margolin Y. et al. Mechanism for the antigonadotropic action of the ovarian gonadotropin-releasing hormone-binding inhibitor protein/histone H2A on ovarian cells. Biol. Reprod. 46: 1021–1026, 1992.

Mathews D. H. et al. Expanded sequence dependence of thermodynamic parameters improves prediction of RNA secondary structure. J. Mol. Biol. 288: 911–940, 1999.

Mathieu E., Meheus L., Raymackers J., and Merregaert J. Characterization of the osteogenic stromal cell line MN7: identification of secreted MN7 proteins using two-dimensional polyacrylamide gel electrophoresis, western blotting and microsequencing. J. Bone Miner. Res. 9; 903–913, 1994.

Mbebi C. et al. Protein nexin I expression is up-regulated in human skeletal muscle by injury-related factors. J. Cell Physiol. 179: 305–314, 1999.

McGrogan et al. (1988) Bio/Technolgoy 6:172–177.

Montague, C.T. et al. Congenital leptin deficiency associated with severe early-onset obesity in humans, Nature, 398: 903–908, 1997.

Ngo (ed) (1988) Nonisotopic immunoassay, Plenum Press, N.Y.

O'Connor, J Neurochem (1991) 56:560 in Oligodeoxynucleotides as Antisense Inhibitors of Gene Expression, CRC Press, Boca Raton, Fla. (1988).

Okabe-Kado J. et al. Effect of histone on induction of differentiation of cultured mouse myeloid leukemia cells. Cancer Res. 41: 1997–2002, 1981.

Perusse, L. et. al. The human obesity gene map: the 1998 update. Obes. Res. 7:111–129, 1999.

Price and Newman (eds) (1991) Principles and practice of immunoassays. Stockton Press, N.Y.

Reichhard R. et al. Preparation of homeostatic thymus hormone consist predominantly of histone 2A and 2B and suggest additional histone function. Proc. Natl. Acad. Sci. USA 82: 4871–4875, 1985.

Ruddy et al. (1997) direct submission.

Ryffel B. et al. Differentiation of human t-lymphoid leukemia onto cells that have a suppressor phenotype is induced by phorbol 12-myristate 13-acetate. Proc. Natl. Acad. Sci. USA 79:7336–7340, 1982.

Sambrook et al. Molecular cloning: A laboratory manual. Cold Spring Harbor Laboratory Press, Plainview, N.Y., 1989

Schreiber, S. L. Target-oriented and diversity-oriented synthesis in drug discovery. Science 287: 1964–1969, 2000.

Schwartz M., et. al. Central nervous system control of food intake, Nature, 404: 661–671, 2000.

Scott R. W. et al. J. Biol. Chem. 58: 10439–10444, 1983.

Semizarov D. et al. A lineage-specific protein kinase crutial for myeloid maturation. Proc. Natl. Acad. Sci. USA 95: 15412–15412, 1998.

Sheehan D. C. Theory and practice of histotechnology, $2^{nd}$ ed. C. V. Mosby Company, St. Louis. 1980, p209.

Smas C. M., and Sul H. S., Biochem. J. 309: 697–710, 1994

Smits P., Poumay Y., Karperien M., Tylzanowski P., Wauters J., Huylebr X., Ponec M., and Merregaert J. Differentiation-dependent alternative splicing and expression of extracellular matrix protein 1 in human keratinocytes. J. Invest. Dermatol. 114:718–724, 2000.

Smits P., Ni J., Feng P., Wauters J., Hul W. V., El Boutaibi M., Dillon P. J., and Merregaet J. The human extracellular matrix gene 1 (ECM1): Genomic structure cDNA localization, expression pattern, and chromosomal location. Genomics 45; 487–495, 1997.

Smyth, M. S. and Martin, J. H. x ray crystalography. Mol. Path. 53: 8–14, 2000.

Sommer J. et al. cDNA sequence coding for a rat glia-derived nexin and its homology to members of the serpin superfamily. Biochem. 26: 6407–6410, 1987.

Spieholz, C. et al. Granulocyte-macrophage colony stimulating factor signals for increased glucose uptake in human melanoma cells. Blood 85: 973–980, 1995.

Stein C. A. Is irrelevant cleavage the price of antisense efficacy? Pharmac. Ther. 85: 231–236, 2000.

Stetler-Stevenson W. G. et al. Tissue inhibitor of metalloproteinase (TIMP-2). A new member of the metalloproteinase inhibitor family. J. Biol. Chem. 264:17374–17378, 1989.

Stites, et al. (eds) Basic and clinical immunology (4th ed), Lange Medical Publication, Los Angeles, Calif.

Strobel A., et al. A leptin missense mutation associated with hypogonadism and morbid obesity, Nature Genet., 18:213–215, 1998.

Thomson, T. M. et al. Differentiation antigens of melanocytes and melanoma cells: analysis of melanosome and cell surface markers of human pigmented cells with monoclonal antibodies. J. Invest. Dermatol. 90: 459–466, 1988.

Tonetti D. A. et al. Protein kinase C-beta is required for macrophage differentiation of human HL-60 leukemia cells. J. Biol. Chem. 269: 23230–23235, 1994.

Varga L. H. et al. Antisense strategies: function and application in immunology. Immun. Lett. 69: 217–224, 1999.

Ward et al. Nature 341: 544–546, 1989.

Watanabe Y. et al. Identification of histone H2A.X as a growth factor secreted by an androgen-independent subline of mouse mammary carcinoma cells. J. Biol. Chem. 271: 25126–25130, 1996.

Wickstrom E. L. et al. Human promyelocytic leukemia HL-60 cell proliferation and c-myc protein expression are inhibited by an antisense pentadecadeoxynucleotide targeted against c-myc MRNA. Proc. Natl. Acad. Sci. USA 85: 1028–1032, 1988.

Wilchek et al. Meth. Enzymol. 104: 3–55, 1984.

World Health Organization, Obesity: Preventing and Managing the Global Epidemic, Geneva, 1998.

Zhong et al. (1983) Nucleic Acids Res. 11(21): 7409–7425.

Zuker, M. Computer prediction of RNA structure. Methods Enzymol. 180: 262–288, 1989.

U.S. Pat. No. 3,817,837
U.S. Pat. No. 3,850,752
U.S. Pat. No. 3,939,350
U.S. Pat. No. 3,996,345
U.S. Pat. No. 4,277,437
U.S. Pat. No. 4,275,149
U.S. Pat. No. 4,366,241
U.S. Pat. No. 4,642,334
U.S. Pat. No. 4,736,866
U.S. Pat. No. 4,816,567
U.S. Pat. No. 4,818,763
U.S. Pat. No. 5,162,215
U.S. Pat. No. 5,489,742
U.S. Pat. No. 5,550,316
U.S. Pat. No. 5,573,933
U.S. Pat. No. 5,614,396
U.S. Pat. No. 5,625,125
U.S. Pat. No. 5,648,061
U.S. Pat. No. 5,741,957
U.S. Pat. No. 5,981,220
U.S. Pat. No. 6,110,723

I claim:

1. An assay for identifying a candidate compound which can modify the lipogenic action of a lipogenin selected from the group consisting of ECM-1, NP-I, TIMP-2 and H2A, said assay comprising;
   (a) obtaining the candidate compound;
   (b) obtaining lipogenic molecules of ECM-1, NP-I, TIMP-2 or H2A or a portion thereof;
   (c) treating target cells by contacting the treated cells wherein said cells are responsive to lipogenic induction, with the compound and the lipogenic molecules; and
   (d) determining if the compound interferes with the lipogenic action of the lipogenins by detecting whether fat droplets form in the target cells, and in what amounts the droplets form relative to control cells that are not treated with the candidate compound.

2. The assay of claim 1, wherein whether fat droplets form in the target cells is determined by a lipid specific stain.

3. The assay of claim 1, wherein determining whether the compound interferes with the lipogenic action of the lipogenins is based on comparison of units of lipogenic activity (ULA) between control and treated cells.

4. The assay of claim 1, wherein the compound modifies the lipogenic action of the lipogenins by inhibiting the action.

* * * * *

SEQUENCE LISTING

<160> NUMBER OF SEQ ID NOS: 13

<210> SEQ ID NO 1
<211> LENGTH: 397
<212> TYPE: PRT
<213> ORGANISM: Homo sapiens

<400> SEQUENCE: 1

```
Met Asn Trp His Leu Pro Leu Phe Leu Leu Ala Ser Val Thr Leu Pro
 1               5                  10                  15

Ser Ile Cys Ser His Phe Asn Pro Leu Ser Leu Glu Glu Leu Gly Ser
            20                  25                  30

Asn Thr Gly Ile Gln Val Phe Asn Gln Ile Val Lys Ser Arg Pro His
        35                  40                  45

Asp Asn Ile Val Ile Ser Pro His Gly Ile Ala Ser Val Leu Gly Met
    50                  55                  60

Leu Gln Leu Gly Ala Asp Gly Arg Thr Lys Lys Gln Leu Ala Met Val
65                  70                  75                  80

Met Arg Tyr Gly Val Asn Gly Val Gly Lys Ile Leu Lys Lys Ile Asn
                85                  90                  95
```

-continued

```
Lys Ala Ile Val Ser Lys Lys Asn Lys Asp Ile Val Thr Val Ala Asn
                100                 105                 110
Ala Val Phe Val Lys Asn Ala Ser Glu Ile Glu Val Pro Phe Val Thr
            115                 120                 125
Arg Asn Lys Asp Val Phe Gln Cys Glu Val Arg Asn Val Asn Phe Glu
        130                 135                 140
Asp Pro Ala Ser Ala Cys Asp Ser Ile Asn Ala Trp Val Lys Asn Glu
145                 150                 155                 160
Thr Arg Asp Met Ile Asp Asn Leu Leu Ser Pro Asp Leu Ile Asp Gly
                165                 170                 175
Val Leu Thr Arg Leu Val Leu Val Asn Ala Val Tyr Phe Lys Gly Leu
            180                 185                 190
Trp Lys Ser Arg Phe Gln Pro Glu Asn Thr Lys Lys Arg Thr Phe Val
        195                 200                 205
Ala Ala Asp Gly Lys Ser Tyr Gln Val Pro Met Leu Ala Gln Leu Ser
        210                 215                 220
Val Phe Arg Cys Gly Ser Thr Ser Ala Pro Asn Asp Leu Trp Tyr Asn
225                 230                 235                 240
Phe Ile Glu Leu Pro Tyr His Gly Glu Ser Ile Ser Met Leu Ile Ala
                245                 250                 255
Leu Pro Thr Glu Ser Ser Thr Pro Leu Ser Ala Ile Ile Pro His Ile
            260                 265                 270
Ser Thr Lys Thr Ile Asp Ser Trp Met Ser Ile Met Val Pro Lys Arg
        275                 280                 285
Val Gln Val Ile Leu Pro Lys Phe Thr Ala Val Ala Gln Thr Asp Leu
    290                 295                 300
Lys Glu Pro Leu Lys Val Leu Gly Ile Thr Asp Met Phe Asp Ser Ser
305                 310                 315                 320
Lys Ala Asn Phe Ala Lys Ile Cys Arg Ser Glu Asn Leu His Val Ser
                325                 330                 335
His Ile Leu Gln Lys Ala Lys Ile Glu Val Ser Glu Asp Gly Thr Lys
            340                 345                 350
Ala Ser Ala Ala Thr Thr Ala Ile Leu Ile Ala Arg Ser Ser Pro Pro
        355                 360                 365
Trp Phe Ile Val Asp Arg Pro Phe Leu Phe Phe Ile Arg His Asn Pro
    370                 375                 380
Thr Gly Ala Val Leu Phe Met Gly Gln Ile Asn Lys Pro
385                 390                 395

<210> SEQ ID NO 2
<211> LENGTH: 130
<212> TYPE: PRT
<213> ORGANISM: Homo sapiens

<400> SEQUENCE: 2

Met Ser Gly Arg Gly Lys Gln Gly Gly Lys Ala Arg Ala Lys Ala Lys
 1               5                  10                  15
Thr Arg Ser Ser Arg Ala Gly Leu Gln Phe Pro Val Gly Arg Val His
            20                  25                  30
Arg Leu Leu Arg Lys Gly Asn Tyr Ala Glu Arg Val Gly Ala Gly Ala
        35                  40                  45
Pro Val Tyr Leu Ala Ala Val Leu Glu Tyr Leu Thr Ala Glu Ile Leu
    50                  55                  60
Glu Leu Ala Gly Asn Ala Ala Arg Asp Asn Lys Lys Thr Arg Ile Ile
65                  70                  75                  80
```

```
Pro Arg His Leu Gln Leu Ala Ile Arg Asn Asp Glu Leu Asn Lys
            85                  90                  95

Leu Leu Gly Lys Val Thr Ile Ala Gln Gly Gly Val Leu Pro Asn Ile
            100                 105                 110

Gln Ala Val Leu Leu Pro Lys Lys Thr Glu Ser His His Lys Ala Lys
            115                 120                 125

Gly Lys
    130

<210> SEQ ID NO 3
<211> LENGTH: 130
<212> TYPE: PRT
<213> ORGANISM: Homo sapiens

<400> SEQUENCE: 3

Met Ser Gly Arg Gly Lys Gln Gly Gly Lys Ala Arg Ala Lys Ala Lys
 1               5                  10                  15

Thr Arg Ser Ser Arg Ala Gly Leu Gln Phe Pro Val Gly Arg Val His
            20                  25                  30

Arg Leu Leu Arg Lys Ala His Tyr Ser Glu Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Leu Asn Lys
            85                  90                  95

Leu Leu Gly Arg Val Thr Ile Ala Gln Gly Gly Val Leu Pro Asn Ile
            100                 105                 110

Gln Ala Val Leu Leu Pro Lys Lys Thr Glu Ser His His Lys Ala Lys
            115                 120                 125

Gly Lys
    130

<210> SEQ ID NO 4
<211> LENGTH: 128
<212> TYPE: PRT
<213> ORGANISM: Homo sapiens

<400> SEQUENCE: 4

Met Ala Gly Gly Lys Ala Gly Lys Asp Ser Gly Lys Ala Lys Thr Lys
 1               5                  10                  15

Ala Val Ser Arg Ser Gln Arg Ala Gly Leu Gln Phe Pro Val Gly Arg
            20                  25                  30

Ile His Arg His Leu Lys Ser Arg Thr Thr Ser His Gly Arg Val Gly
        35                  40                  45

Ala Thr Ala Ala Val Tyr Ser Ala Ala Ile Leu Glu Tyr Leu Thr Ala
    50                  55                  60

Glu Val Leu Glu Leu Ala Gly Asn Ala Ser Lys Asp Leu Lys Val Lys
65                  70                  75                  80

Arg Ile Thr Pro Arg His Leu Gln Leu Ala Ile Arg Gly Asp Glu Glu
            85                  90                  95

Leu Asp Ser Leu Ile Lys Ala Thr Ile Ala Gly Gly Gly Val Ile Pro
            100                 105                 110

His Ile His Lys Ser Leu Ile Gly Lys Lys Gly Gln Gln Lys Thr Val
            115                 120                 125
```

```
<210> SEQ ID NO 5
<211> LENGTH: 143
<212> TYPE: PRT
<213> ORGANISM: Homo sapiens

<400> SEQUENCE: 5

Met Ser Gly Arg Gly Lys Thr Gly Lys Ala Arg Ala Lys Ala Lys
 1               5                  10                  15

Ser Arg Ser Ser Arg Ala Gly Leu Gln Phe Pro Val Gly Arg Val His
                20                  25                  30

Arg Leu Leu Arg Lys Gly His Tyr Ala Glu Arg Val Gly Ala Gly Ala
            35                  40                  45

Pro Val Tyr Leu Ala Ala Val Leu Glu Tyr Leu Thr Ala Glu Ile Leu
        50                  55                  60

Glu Leu Ala Gly Asn Ala Ala Arg Asp Asn Lys Lys Thr Arg Ile Ile
 65                 70                  75                  80

Pro Arg His Leu Gln Leu Ala Ile Arg Asn Asp Glu Glu Leu Asn Lys
                85                  90                  95

Leu Leu Gly Gly Val Thr Ile Ala Gln Gly Gly Val Leu Pro Asn Ile
            100                 105                 110

Gln Ala Val Leu Leu Pro Lys Lys Thr Ser Ala Thr Val Gly Pro Lys
        115                 120                 125

Ala Pro Ser Gly Lys Lys Ala Thr Gln Ala Ser Gln Glu Tyr
    130                 135                 140

<210> SEQ ID NO 6
<211> LENGTH: 130
<212> TYPE: PRT
<213> ORGANISM: Homo sapiens

<400> SEQUENCE: 6

Met Ser Gly Arg Gly Lys Gln Gly Gly Lys Ala Arg Ala Lys Ala Lys
 1               5                  10                  15

Ser Arg Ser Ser Arg Ala Gly Leu Gln Phe Pro Val Gly Arg Val His
                20                  25                  30

Arg Leu Leu Arg Lys Gly Asn Tyr Ala Glu Arg Val Gly Ala Gly Ala
            35                  40                  45

Pro Val Tyr Met Ala Ala Val Leu Glu Tyr Leu Thr Ala Glu Ile Leu
        50                  55                  60

Glu Leu Ala Gly Asn Ala Ala Arg Asp Asn Lys Lys Thr Arg Ile Ile
 65                 70                  75                  80

Pro Arg His Leu Gln Leu Ala Ile Arg Asn Asp Glu Glu Leu Asn Lys
                85                  90                  95

Leu Leu Gly Lys Val Thr Ile Ala Gln Gly Gly Val Leu Pro Asn Ile
            100                 105                 110

Gln Ala Val Leu Leu Pro Lys Lys Thr Glu Ser His His Lys Ala Lys
        115                 120                 125

Gly Lys
    130

<210> SEQ ID NO 7
<211> LENGTH: 130
<212> TYPE: PRT
<213> ORGANISM: Homo sapiens

<400> SEQUENCE: 7

Met Ser Gly Arg Gly Lys Gln Gly Gly Lys Ala Arg Ala Lys Ala Lys
 1               5                  10                  15
```

```
Ser Arg Ser Ser Arg Ala Gly Leu Gln Phe Pro Val Gly Arg Val His
            20                  25                  30

Arg Leu Leu Arg Lys Gly Asn Tyr Ala Glu Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
 65                  70                  75                  80

Pro Arg His Leu Gln Leu Ala Ile Arg Asn Asp Glu Glu Leu Asn Lys
                85                  90                  95

Leu Leu Gly Arg Val Thr Ile Ala Gln Gly Gly Val Leu Pro Asn Ile
            100                 105                 110

Gln Ala Val Leu Leu Pro Lys Lys Thr Glu Ser His His Lys Ala Lys
        115                 120                 125

Gly Lys
    130

<210> SEQ ID NO 8
<211> LENGTH: 130
<212> TYPE: PRT
<213> ORGANISM: Homo sapiens

<400> SEQUENCE: 8

Met Ser Gly Arg Gly Lys Gln Gly Gly Lys Ala Arg Ala Lys Ala Lys
 1               5                  10                  15

Thr Arg Ser Ser Arg Ala Gly Leu Gln Phe Pro Val Gly Arg Val His
            20                  25                  30

Arg Leu Leu Arg Lys Gly Asn Tyr Ala Glu Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
 65                  70                  75                  80

Pro Arg His Leu Gln Leu Ala Ile Arg Asn Asp Glu Glu Leu Asn Lys
                85                  90                  95

Leu Leu Gly Lys Val Thr Ile Ala Gln Gly Gly Val Leu Pro Asn Ile
            100                 105                 110

Gln Ala Val Leu Leu Pro Lys Lys Thr Glu Ser His His Lys Ala Lys
        115                 120                 125

Gly Lys
    130

<210> SEQ ID NO 9
<211> LENGTH: 130
<212> TYPE: PRT
<213> ORGANISM: Homo sapiens

<400> SEQUENCE: 9

Met Ser Gly Arg Gly Lys Gln Gly Gly Lys Ala Arg Ala Lys Ala Lys
 1               5                  10                  15

Thr Arg Ser Ser Arg Ala Gly Leu Gln Phe Pro Val Gly Arg Val His
            20                  25                  30

Arg Leu Leu Arg Lys Gly Asn Tyr Ala Glu Arg Val Gly Ala Gly Ala
        35                  40                  45

Pro Val Tyr Leu Ala Ala Val Leu Glu Tyr Leu Thr Ala Glu Ile Leu
    50                  55                  60
```

```
Glu Leu Ala Gly Asn Ala Ala Arg Asp Asn Lys Lys Thr Arg Ile Ile
 65                  70                  75                  80

Pro Arg His Leu Gln Leu Ala Ile Arg Asn Asp Glu Glu Leu Asn Lys
                 85                  90                  95

Leu Leu Gly Lys Val Thr Ile Ala Gln Gly Gly Val Leu Pro Asn Ile
            100                 105                 110

Gln Ala Val Leu Leu Pro Lys Lys Thr Glu Ser His His Lys Ala Lys
        115                 120                 125

Gly Lys
    130

<210> SEQ ID NO 10
<211> LENGTH: 130
<212> TYPE: PRT
<213> ORGANISM: Homo sapiens

<400> SEQUENCE: 10

Met Ser Gly Arg Gly Lys Gln Gly Gly Lys Ala Arg Ala Lys Ala Lys
  1               5                  10                  15

Thr Arg Ser Ser Arg Ala Gly Leu Gln Phe Pro Val Gly Arg Val His
                 20                  25                  30

Arg Leu Leu Arg Lys Gly Asn Tyr Ala Glu Arg Val Gly Ala Gly Ala
            35                  40                  45

Pro Val Tyr Leu Ala Ala Val Leu Glu Tyr Leu Thr Ala Glu Ile Leu
     50                  55                  60

Glu Leu Ala Gly Asn Ala Ala Arg Asp Asn Lys Lys Thr Arg Ile Ile
 65                  70                  75                  80

Pro Arg His Leu Gln Leu Ala Ile Arg Asn Asp Glu Glu Leu Asn Lys
                 85                  90                  95

Leu Leu Gly Lys Val Thr Ile Ala Gln Gly Gly Val Leu Pro Asn Glu
            100                 105                 110

Gln Ala Val Leu Leu Pro Lys Lys Thr Glu Ser His His Lys Ala Lys
        115                 120                 125

Gly Lys
    130

<210> SEQ ID NO 11
<211> LENGTH: 220
<212> TYPE: PRT
<213> ORGANISM: Homo sapiens

<400> SEQUENCE: 11

Met Gly Ala Ala Ala Arg Thr Leu Arg Leu Ala Leu Gly Leu Leu Leu
  1               5                  10                  15

Leu Ala Thr Leu Leu Arg Pro Ala Asp Ala Cys Ser Cys Ser Pro Val
                 20                  25                  30

His Pro Gln Gln Ala Phe Cys Asn Ala Asp Val Val Ile Arg Ala Lys
            35                  40                  45

Ala Val Ser Glu Lys Glu Val Asp Ser Gly Asn Asp Ile Tyr Gly Asn
     50                  55                  60

Pro Ile Lys Arg Ile Gln Tyr Glu Ile Lys Gln Ile Lys Met Phe Lys
 65                  70                  75                  80

Gly Pro Glu Lys Asp Ile Glu Phe Ile Tyr Thr Ala Pro Ser Ser Ala
                 85                  90                  95

Val Cys Gly Val Ser Leu Asp Val Gly Gly Lys Lys Glu Tyr Leu Ile
            100                 105                 110
```

Ala Gly Lys Ala Glu Gly Asp Gly Lys Met His Ile Thr Leu Cys Asp
         115                 120                 125

Phe Ile Val Pro Trp Asp Thr Leu Ser Thr Thr Gln Lys Lys Ser Leu
     130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
             180                 185                 190

Cys Ile Lys Arg Ser Asp Gly Ser Cys Ala Trp Tyr Arg Gly Ala Ala
         195                 200                 205

Pro Pro Lys Gln Glu Phe Leu Asp Ile Glu Asp Pro
     210                 215                 220

<210> SEQ ID NO 12
<211> LENGTH: 1075
<212> TYPE: DNA
<213> ORGANISM: Homo sapiens

<400> SEQUENCE: 12
cgcagcaaac acatccgtag aaggcagcgc ggccgccgag agccgcagcg ccgctcgccc     60 gccgccccc accccgccgc cccgcccggc gaattgcgcc ccgcgcccct cccctcgcgc    120
ccccgagaca aagaggagag aaagtttgcg cggccgagcg gggcaggtga ggagggtgag    180
ccgcgcggga ggggcccgcc tcggccccgg ctcagccccc gccgcgcccc ccagcccgcc    240
gccgcgagca gcgcccggac cccccagcgg cggcccccgc ccgcccagcc cccggcccg    300 ccatgggcgc cgcggcccgc accctgcggc tggcgctcgg cctcctgctg ctggcgacgc    360
tgcttcgccc ggccgacgcc tgcagctgct ccccggtgca cccgcaacag gcgttttgca    420
atgcagatgt agtgatcagg gccaaagcgg tcagtgagaa ggaagtggac tctggaaacg    480
acatttatgg caaccctatc aagaggatcc agtatgagat caagcagata agatgttca    540 aagggcctga gaaggatata gagtttatct acacggcccc ctcctcggca gtgtgtgggg    600
tctcgctgga cgttggagga aagaaggaat atctcattgc aggaaaggcc gagggggacg    660
gcaagatgca catcaccctc tgtgacttca tcgtgccctg ggacaccctg agcaccaccc    720
agaagaagag cctgaaccac aggtaccaga tgggctgcga gtgcaagatc acgcgctgcc    780
ccatgatccc gtgctacatc tcctccccgg acgagtgcct ctggatggac tgggtcacag    840
agaagaacat caacgggcac caggccaagt tcttcgcctg catcaagaga agtgacggct    900
cctgtgcgtg gtaccgcggc gcggcgcccc ccaagcagga gtttctcgac atcgaggacc    960
cataagcagg cctccaacgc ccctgtggcc aactgcaaaa aaagcctcca agggtttcga   1020
ctggtccagc tctgacatcc cttcctggaa acagcatgaa taaaacactc atccc         1075

<210> SEQ ID NO 13
<211> LENGTH: 540
<212> TYPE: PRT
<213> ORGANISM: Homo sapiens

<400> SEQUENCE: 13

Met Gly Thr Thr Ala Arg Ala Ala Leu Val Leu Thr Tyr Leu Ala Val
 1               5                  10                  15

Ala Ser Ala Ala Ser Glu Gly Gly Phe Thr Ala Thr Gly Gln Arg Gln
             20                  25                  30

-continued

```
Leu Arg Pro Glu His Phe Gln Glu Val Gly Tyr Ala Ala Pro Pro Ser
        35                  40                  45

Pro Pro Leu Ser Arg Ser Leu Pro Met Asp His Pro Asp Ser Ser Gln
    50                  55                  60

His Gly Pro Pro Phe Glu Gly Gln Ser Gln Val Gln Pro Pro Pro Ser
65                  70                  75                  80

Gln Glu Ala Thr Pro Leu Gln Gln Glu Lys Leu Leu Pro Ala Gln Leu
                85                  90                  95

Pro Ala Glu Lys Glu Val Gly Pro Pro Leu Pro Gln Glu Ala Val Pro
            100                 105                 110

Leu Gln Lys Glu Leu Pro Ser Leu Gln His Pro Asn Glu Gln Lys Glu
        115                 120                 125

Gly Thr Pro Ala Pro Phe Gly Asp Gln Ser His Pro Glu Pro Glu Ser
    130                 135                 140

Trp Asn Ala Ala Gln His Cys Gln Gln Asp Arg Ser Gln Gly Gly Trp
145                 150                 155                 160

Gly His Arg Leu Asp Gly Phe Pro Pro Gly Arg Pro Ser Pro Asp Asn
                165                 170                 175

Leu Asn Gln Ile Cys Leu Pro Asn Arg Gln His Val Val Tyr Gly Pro
            180                 185                 190

Trp Asn Leu Pro Gln Ser Ser Tyr Ser His Leu Thr Arg Gln Gly Glu
        195                 200                 205

Thr Leu Asn Phe Leu Glu Ile Gly Tyr Ser Arg Cys Cys His Cys Arg
    210                 215                 220

Ser His Thr Asn Arg Leu Glu Cys Ala Lys Leu Val Trp Glu Glu Ala
225                 230                 235                 240

Met Ser Arg Phe Cys Glu Ala Glu Phe Ser Val Lys Thr Arg Pro His
                245                 250                 255

Trp Cys Cys Thr Arg Gln Gly Glu Ala Arg Phe Ser Cys Phe Gln Glu
            260                 265                 270

Glu Ala Pro Gln Pro His Tyr Gln Leu Arg Ala Cys Pro Ser His Gln
        275                 280                 285

Pro Asp Ile Ser Ser Gly Leu Glu Leu Pro Phe Pro Pro Gly Val Pro
    290                 295                 300

Thr Leu Asp Asn Ile Lys Asn Ile Cys His Leu Arg Arg Phe Arg Ser
305                 310                 315                 320

Val Pro Arg Asn Leu Pro Ala Thr Asp Pro Leu Gln Arg Glu Leu Leu
                325                 330                 335

Ala Leu Ile Gln Leu Glu Arg Gly Phe Gln Arg Cys Cys Arg Gln Gly
            340                 345                 350

Asn Asn His Thr Cys Thr Trp Lys Ala Trp Glu Asp Thr Leu Asp Lys
        355                 360                 365

Tyr Cys Asp Arg Glu Tyr Ala Val Lys Thr His His Leu Cys Cys
    370                 375                 380

Arg His Pro Pro Ser Pro Thr Arg Asp Glu Cys Phe Ala Arg Arg Ala
385                 390                 395                 400

Pro Tyr Pro Asn Tyr Asp Arg Asp Ile Leu Thr Ile Asp Ile Ser Arg
                405                 410                 415

Val Thr Pro Asn Leu Met Gly His Leu Cys Gly Asn Gln Arg Val Leu
            420                 425                 430

Thr Lys His Lys His Ile Pro Gly Leu Ile His Asn Met Thr Ala Arg
        435                 440                 445
```

```
-continued

Cys Cys Asp Leu Pro Phe Pro Glu Gln Ala Cys Cys Ala Glu Glu Glu
    450             455                 460

Lys Leu Thr Phe Ile Asn Asp Leu Cys Gly Pro Arg Arg Asn Ile Trp
465                 470                 475                 480

Arg Asp Pro Ala Leu Cys Cys Tyr Leu Ser Pro Gly Asp Glu Gln Val
                485                 490                 495

Asn Cys Phe Asn Ile Asn Tyr Leu Arg Asn Val Ala Leu Val Ser Gly
            500                 505                 510

Asp Thr Glu Asn Ala Lys Gly Gln Gly Glu Gln Gly Ser Thr Gly Gly
        515                 520                 525

Thr Asn Ile Ser Ser Thr Ala Glu Pro Lys Glu Glu
    530             535                 540
```